(12) United States Patent
Bonde

(10) Patent No.: US 7,416,644 B2
(45) Date of Patent: Aug. 26, 2008

(54) METHOD AND DEVICE FOR STRIPPING AMMONIA FROM LIQUIDS

(75) Inventor: Torben A. Bonde, Egaa (DK)

(73) Assignee: Green Farm Energy, Randers (DK)

( * ) Notice: Subject to any disclaimer, the term of this patent is extended or adjusted under 35 U.S.C. 154(b) by 259 days.

(21) Appl. No.: 10/522,885

(22) PCT Filed: Aug. 1, 2003

(86) PCT No.: PCT/DK03/00520

§ 371 (c)(1), (2), (4) Date: Feb. 1, 2005

(87) PCT Pub. No.: WO2004/012840

PCT Pub. Date: Feb. 12, 2004

(65) Prior Publication Data

US 2006/0006055 A1 Jan. 12, 2006

(30) Foreign Application Priority Data

Aug. 1, 2002 (DK) ................ 2002 01172

(51) Int. Cl.
*B01D 3/38* (2006.01)
*B01D 5/00* (2006.01)
*C01C 3/00* (2006.01)
*B01D 3/00* (2006.01)

(52) U.S. Cl. ............... 203/14; 203/42; 203/79; 203/80; 203/87; 203/95; 423/351; 423/352; 435/289.1; 202/155; 202/186

(58) Field of Classification Search .......... 203/14, 203/42, 73, 79, 80, 87, 95; 202/154, 155, 202/186; 423/351, 352; 95/149, 267, 288; 435/289.1

See application file for complete search history.

(56) References Cited

U.S. PATENT DOCUMENTS 4,041,182 A   8/1977   Erickson et al.

(Continued)

FOREIGN PATENT DOCUMENTS

DE   3603739   8/1986

(Continued)

OTHER PUBLICATIONS

Chang, et al., "Lime Pretreatment of Switchgrass", *Applied Biochemistry and Biotechnology*, vol. 63-65, pp. 3-19, 1997.

(Continued)

*Primary Examiner*—Virginia Manoharan
(74) *Attorney, Agent, or Firm*—Iver P. Cooper

(57) ABSTRACT

The present invention provides a method and a system for stripping volatile compounds such as ammonia from liquids. Part of the ammonia is stripped from the liquid in a system having a shunt through which liquid such as e.g. fermented biomass can be diverted in the form of a side stream in liquid contact with a main fermentor(s). The stripper system is connected to an evaporator. In the evaporator aqueous liquid is heated at a pressure below atmospheric pressure whereby vapor is developed at a temperature below 100° C. The vapor from the evaporator is directed to the liquid medium containing ammonia and this results in ammonia being stripped from the liquid and transferred to the vapor phase. The vapor phase is condensed in a first condenser at a low pressure, and the liquid thus obtained is further treated in a stripper unit at a higher pressure.

94 Claims, 7 Drawing Sheets

U.S. PATENT DOCUMENTS

| | | | |
|---|---|---|---|
| 4,100,023 A | 7/1978 | McDonald | |
| 4,246,417 A | 1/1981 | Tsao | |
| 4,323,430 A | 4/1982 | Glassman et al. | |
| 4,329,428 A | 5/1982 | Ghosh et al. | |
| 4,579,654 A | 4/1986 | Bremmer | |
| 4,640,740 A * | 2/1987 | Moore et al. | 159/13.1 |
| 4,668,250 A | 5/1987 | Drese | |
| 4,750,454 A | 6/1988 | Santina et al. | |
| 4,801,356 A | 1/1989 | Grasso | |
| 5,071,559 A | 12/1991 | Bleeker | |
| 5,275,701 A * | 1/1994 | Mazzafro et al. | 203/12 |
| 5,296,147 A | 3/1994 | Koster et al. | |
| 5,389,258 A | 2/1995 | Smis et al. | |
| 5,494,587 A | 2/1996 | Morlec et al. | |
| 5,525,229 A | 6/1996 | Shih | |
| 5,593,590 A | 1/1997 | Steyskal | |
| 5,616,163 A | 4/1997 | Halfter | |
| 5,656,059 A | 8/1997 | Monster et al. | |
| 5,670,047 A | 9/1997 | Burke | |
| 5,681,481 A | 10/1997 | Christy et al. | |
| 5,746,919 A | 5/1998 | Dague et al. | |
| 5,773,526 A | 6/1998 | Van Dijk et al. | |
| 5,782,950 A | 7/1998 | Kanitz et al. | |
| 5,783,073 A | 7/1998 | Christy et al. | |
| 5,851,404 A | 12/1998 | Christy et al. | |
| 5,853,450 A | 12/1998 | Burnham et al. | |
| 5,863,434 A | 1/1999 | Masse et al. | |
| 6,071,418 A | 6/2000 | Tai | |
| 6,171,499 B1 | 1/2001 | Bouchalat | |

FOREIGN PATENT DOCUMENTS

| | | |
|---|---|---|
| DE | 3737747 | 5/1989 |
| DE | 4201166 | 7/1993 |
| DE | 4239637 | 4/1994 |
| DE | 4324410 | 8/1994 |
| DE | 4444032 | 5/1996 |
| DE | 19623163 | 12/1996 |
| DE | 19625288 | 1/1997 |
| DE | 19615063 | 9/1997 |
| DE | 19628521 | 1/1998 |
| DE | 19644613 | 4/1998 |
| DE | 19809299 | 9/1999 |
| DE | 19828889 | 12/1999 |
| EP | 0218896 | 4/1987 |
| EP | 0286115 | 10/1988 |
| EP | 0351922 | 1/1990 |
| EP | 0866042 | 9/1998 |
| EP | 1021958 | 7/2000 |
| ES | 2100123 | 6/1997 |
| FR | 2576741 | 8/1986 |
| FR | 2711980 | 5/1995 |
| GB | 2013170 | 8/1979 |
| JP | 53029278 | 3/1978 |
| JP | 57012896 | 1/1982 |
| JP | 59039395 | 3/1984 |
| JP | 2001113265 | 4/2001 |
| SE | 17615 | 6/1997 |
| WO | 8400038 | 1/1984 |
| WO | 8900548 | 1/1989 |
| WO | 9102582 | 3/1991 |
| WO | 9942423 | 8/1999 |
| WO | 02053878 | 7/2002 |

OTHER PUBLICATIONS www.uni-hohenheim.de/i3ve/00217110/01492041.htm, "Cofermentation of liquid manure and beets as a regenerative energy", Jun. 20, 2003.

www.uni-hohenheim.de/i2ve/00217110/01488041.htm, "Nutrient transport and separation behaviour during liquid-solid-separation of liquid manure", Apr. 27, 2005.

Basegra, et al., www.biogas.ch/f+e/grasbasi.htm, "Digestion of 'energy grass'", Jun. 20, 2003.

Edelmann, et al., www.biogas.ch/f+e/2stede.htm, "Two step anaerobic digestion of biogenic solid wastes", Jun. 20, 2003.

www.biogas.ch/f+e/hygiene.htm, "Hygienic considerations concerning co-digestion of MSW in agricultural biogas plants", Jun. 20, 2003.

Engeli, et al., www.biogas.ch/f+e/memen.htm, "Membrane treatment of effluents from anaerobic digestion of solid waste", Jan. 24, 2001.

riera.ceeeta.pt/images/ukbio_mass.htm, "Anaerobic Digestion & Biogas", Jan. 24, 2001.

Liao, et al., "Removal of nitrogen from swine manure wastewaters by ammonia stripping", www.nal.usda.gov/wgic/Bibliographies/swine2.htm.

www.igb.fhg.de/UWbio/en/Manure.en.html, "Environmentally friendly reprocessing and utilization of liquid manure".

* cited by examiner

Fig. 7  Flow diagram
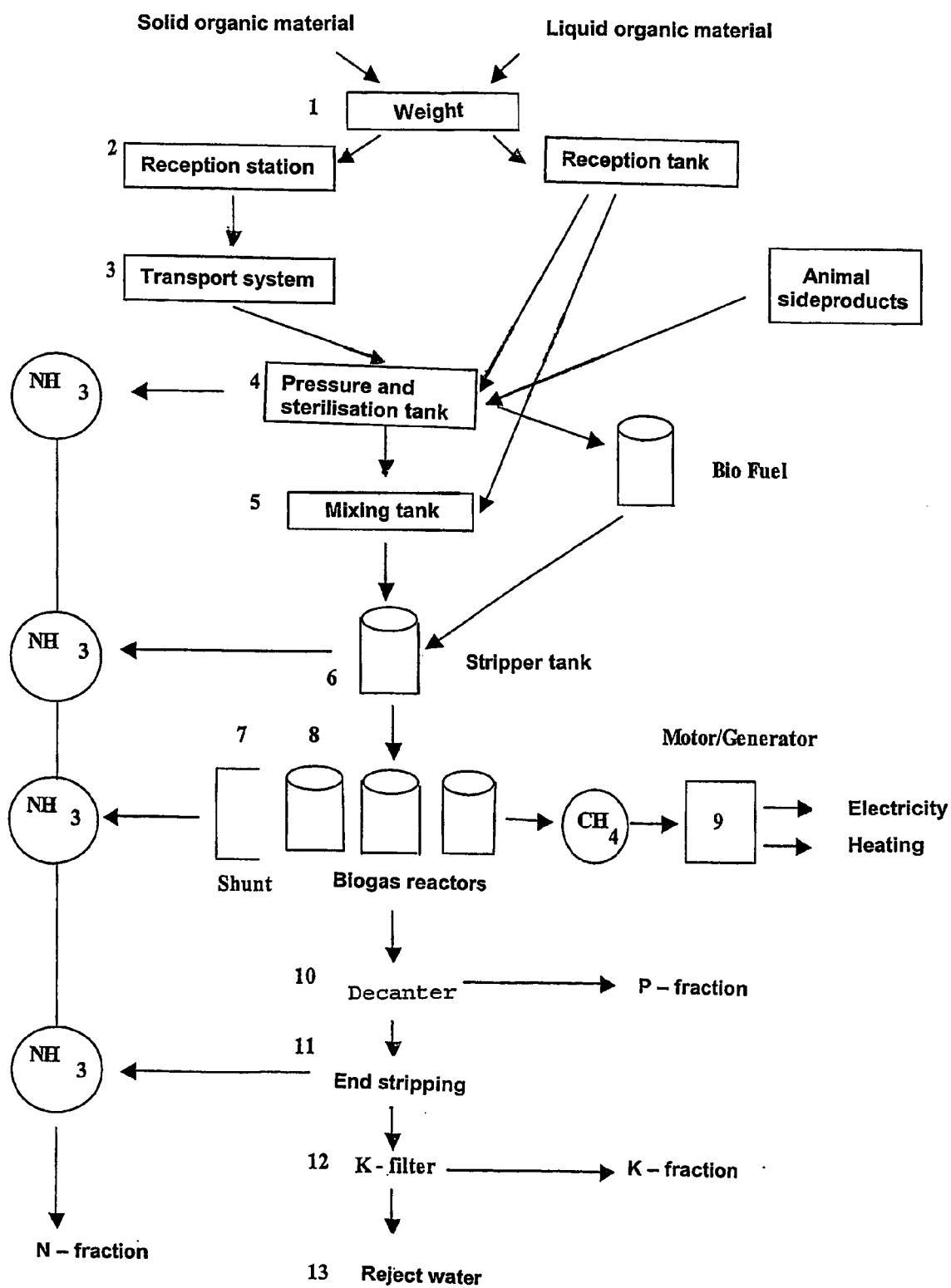

METHOD AND DEVICE FOR STRIPPING AMMONIA FROM LIQUIDS

FIELD OF THE INVENTION

The present invention relates to a method for stripping off ammonia from liquids by contacting said liquids with vapour at low pressure or under vacuum, a system comprising a shunt and a stripper device in which the ammonia is stripped from the liquid medium comprising ammonia, a mobile unit comprising such a system, and a plant wherein a liquid medium comprising ammonia is generated during e.g. fermentation, wherein said plant comprises said system for stripping ammonia from the liquid. Ammonia comprising liquids generated during operation of e.g. biogas plants can be handled by the system.

BACKGROUND OF THE INVENTION

Industrial plants for production of sugars, alcohols, industrial enzymes, medicaments and the like as well as different energy plants for production of renewable energy from biomass is usually based on the activity of microorganisms under either aerobic or anaerobic conditions in process tanks. Examples are the production of insulin and beverages by yeast under anaerobic conditions in fermentation tanks where the substrate is malt or molasses, or a similar agricultural plant product rich in carbohydrates.

The treatment of waste is another area widely accepted as a proven technology and extensively used. Also in this case microorganisms in aerobic/anaerobic process tanks digest the waste. However, not only municipal sewage waste but also a number of various industrial and agricultural wastes are also treated through microbiological means.

The microbial activity is based on the growth kinetics of the different groups of microorganisms involved and of the activity of a number of specific enzymes necessary to perform the biochemical processes. The overall result of the processes is microbial growth, substrate consumption, and product formation. However, enzymes and microorganisms may be inhibited by the main products or side products, which accumulate in the process tank or any other substance resulting from the microbial transformations of the substrate. Also substances in the biomass or the substrate in it self may hamper optimal performance of the bioreactor. Such inhibition may lead to a substantially lower microbial activity and thus substantially lower production and perhaps a complete break down of the microbial process if the inhibitory substances are not carefully controlled.

Such risks are usually avoided or controlled by managing the substrate loading or the organic loading rate, the rate being set to ensure a concentration of the critical component below levels unacceptable to the process. Other process parameters such as temperature, pH, salinity, media composition, and the microbial consortia employed may also be selected according to the process optima. However, managing the organic loading rate at low inputs to the bioreactors inevitably result in low product formation and a poor performance of the process in general. The control of the other process parameters such as temperature and pH compensates only partly for the inhibition by the inhibitory substance or substances. A direct control of the inhibitory substance at levels sub critical to the process is far the most effective control if possible.

It is often desirable to remove volatile components from microbial process tanks during continued operation of the process, i.e. the inhibitory substance is continuously removed yet the process and the microorganisms are left unaffected.

Generally, volatile components can be separated from a liquid by air stripping or vapor stripping, such as e.g. steam stripping of ammonia from aqueous solutions, or e.g. steam stripping of methanol.

Methods and systems for vapor stripping of volatile components from liquids comprise steps and means for producing a vapor of volatile components, such as ammonia, from the liquid. Typically, evaporation means requires energy from a suitable heating medium, typically a heating medium of high value such as e.g. electricity or combustion fuel, whereas available on-site heating media often are low-valued heating media such as cooling media comprising otherwise wasted heat from e.g. combustion of organic waste gases in an engine.

For effective removal of volatile components from liquids at atmospheric pressure, large amounts of steam or heat are required. Consequently, typical vapor stripping apparatus comprises large, energy consuming, and expensive components, which are not suited for small in-situ liquid treatment systems, such as system for treatment of liquids of manure at animal farming sites.

U.S. Pat. Nos. 5,385,646, 5,498,317, 5,643,420 and 5,779,861 disclose an apparatus and method for treating process condensate from a chemical production plant wherein contaminants are substantially removed from a condensate by steam stripping and subsequent rectification in a relatively low pressure stripping/-rectification tower. A portion of condensed overhead and scrubbing aqueous liquid-containing contaminants is returned to the top of the rectification section of the tower as reflux and the balance is withdrawn as a concentrated steam.

DE 43 24 410 C1 discloses a method of removing ammonia from waste aqueous liquid of a biological waste treatment plant, the method consisting of a two step process: a first step comprising stripping ammonia from the waste aqueous liquid by steam at atmospheric pressure, condensing said steam comprising stripped ammonia, and producing condensation heat for producing said steam; and a second step comprising rectifying said condensed steam comprising ammonia to at least 20% by weight of aqueous ammonia, said second step advantageously being carried out at a pressure above atmospheric pressure.

SUMMARY OF THE INVENTION

There is a need for an improved method and an apparatus for separation of volatile components from a liquid, which method and apparatus is simple and economic in operation allowing low-valued heating media to be used, and which method and apparatus avoid large, energy consuming, and expensive components.

The present invention aims to remove undesirable or inhibitory volatile components from microbial process tanks during continued operation of the process. The inhibitory substance is continuously removed and the process and the microorganisms are left unaffected.

Although anaerobic digestion of agricultural waste such as animal manures is well established, the digestion of swine slurry is difficult due to a high content of ammonia in the manure and a relatively small content of solids. The solids consist of complex carbohydrates mainly including small amounts of proteins and fats.

The inhibition by ammonia is substantial at contents of more than approximately 1 kg free ammonia-N per tonnes swine slurry, where free ammonia-N is $NH_3$ (s) and not the dissolved ammonia ion $NH_4^+$ (s). The concentration of gaseous ammonia $NH_3$ (g) is under normal circumstances much lower than the NH$_3$ (s) concentration. The concentration of free ammonia is a function of temperature and pH. For example, at a total N-content of 6 kg per tonnes swine slurry the concentration of free ammonia at pH 8 is about 0.75 kg/tons at 37° C., 1.4 kg/tons at 45° C., 1.6 kg/tons at 55° C., and 2.6 kg/tons at 60° C. (e.g. Hansen K. V., 1. Angelidaki, B. K. Ahring (1998) Anaerobic digestion of swine manure: Inhibition by ammonia. Aqueous liquid Research 32. 5-12).

The swine slurry is therefore in conventional systems often mixed with cattle slurry or other biomasses rich in carbohydrates to achieve a biomass mixture, which is easier to digest. The operating temperature is also often set at mesophile temperatures about 45° C. or lower, where the free ammonia content is relatively small. However, the efficiency of such schemes is relatively low.

A far higher efficiency would be achieved if the ammonia content was monitored and controlled by continuously removing ammonia above a certain threshold value. This would enable the process to be run at thermophilic temperatures around 60° C. where the microbial activity is much higher.

As a rule of thump the microbial activity doubles for each 10s increase of temperature. If ammonia could be controlled, it would be preferable to operate biogas plants at about 60° C. (e.g. Ahring B. K., A. A. Ibrahim, Z. Mladenovska (2001) Effect of temperature increases from 55 to 65° C. on performance and microbial population dynamics of an anaerobic reactor treating cattle manure. Aqueous liquid Research 35. 2446-2452).

Several biogas plants co-digest animal manures and industrial waste or other biomasses in order to achieve a biogas production, which render the enterprise economical in terms of reasonable pay back times and revenue. It is in general not possible to arrive at a sound economy for plants digesting animal manures only and addition of supplementary biomasses are therefore necessary. However, several biomasses of agricultural origin contain large amounts of proteins or ammonia and these substrates are therefore difficult to co-digest with animal manures in any significant quantities. Such biomasses include animal bi-products, such as meat and bone meal, vegetable proteins, as well as molasses and vinasse and similar products.

One particularly interesting animal bi-product is meat and bone meal. Meat and bone meal contains between 55-60% protein, 7-14% lipids, and 2-5% aqueous liquid so approximately 9% of the meat and bone meal is nitrogen. One tonnes of meat and bone meal thus contains approximately 90 kg N.

A typical N-content in animal manure is about 6 kg N per tonnes slurry and the critical content is 4-6 kg N per tonnes. Higher amounts inevitably leads to break-down of the process, which is already hampered at the 6 kg N per tonnes. Addition of e.g. 5% meat and bone meal would add 4.5 kg N per tonnes slurry and it has so far been possible to add only very small percentages of about 2.5% of meat and bone meal to animal slurries, which are to be digested in biogas plants. However, by continuously removing the liberated ammonia as disclosed by the present invention it is possible to add e.g. a 10-fold amount of 25% meat and bone meal and thus benefit from the biogas potential of the meat and bone meal, while concentrating the ammonia in a separate fraction well suited as fertilizer.

Even though the ammonia content of a particular substrate can also be removed before degassing in the biogas reactor, substrates with high protein contents release their nitrogen content as ammonia within the bioreactor during the digestion and thus during the methane formation from the substrate. A pre bioreactor removal of ammonia from the N comprising substrates including proteins is therefore not always sufficient. However, the present invention allows a continuous removal of ammonia generated during fermentation within the bioreactor. Any content of ammonia already present in the influent may also be removed by the method and system of the invention. The present invention in a first aspect provides a method and a system for stripping ammonia from liquid medium comprising ammonia or precursors thereof, such as e.g. liquids in biogas reactors. Part of the ammonia is stripped from the liquid in a stripper system comprising a shunt through which liquid such as e.g. fermentation medium comprising a biomass can be diverted in the form of a side stream in liquid contact with a main fermentor(s). The stripper system is connected to an evaporator. In the evaporator aqueous liquid is heated at a pressure below atmospheric pressure whereby vapor is developed at a temperature below 100° C.

The vapor from the evaporator is directed to the liquid medium comprising ammonia and this results in ammonia being stripped from the liquid and transferred to the vapor phase. The vapor phase is condensed in a first condenser at a low pressure, e.g. a pressure below 1 bar, such as a pressure of less than 0.5 bar, and the liquid thus obtained can be further treated in a stripper unit at a high pressure, such as e.g. a pressure at or above 1 bar, but preferably below 5 bar, said treatment resulting in the generation of a more concentrated ammonia comprising fluid or liquid. When stripped for at least a substantial part of the ammonia the liquid initially obtained from the biogas reactor and diverted to the shunt can be returned to the reactor.

Definitions

Cold steam means steam at a temperature below 100° C. and at a pressure below 1 bar. As an example, cold steam can be generated by e.g. heating aqueous liquid to about 50-80° C. and lowering the pressure above the aqueous liquid surface to 0.1 to 0.3 bar, whereby a steam is obtained.

Hot steam means steam generated at a pressure of 1 bar or more.

NH$_3$ (g) means NH$_3$ in gaseous phase

NH$_3$ (s) means NH$_3$ in soluble (liquid) phase

NH$_4^+$ (s) means NH$_4^+$ in soluble (liquid) phase

Vapor stripping means stripping of volatile compounds from a media by directing vapor through the medium.

Shunt is a device to which fermentation/reactor liquids can be shunted and wherein volatile compounds comprised in said liquids can be stripped off by using cold steam, i.e. steam at a temperature below 100° C. and at pressure below a predetermined reference pressure such as e.g. 1 bar.

Stripper unit is a device wherein volatile compounds can be stripped off a liquid at a pressure at or above a predetermined reference pressure such as e.g. 1 bar.

DETAILED DESCRIPTION OF THE DRAWINGS

FIG. 1 illustrates the stripper device and the main process steps according to one preferred embodiment of the invention. The figure illustrates a biogas reactor (R), a shunt (S), an evaporator (E), a stripper unit (K3), a first condensing device (K1), a further optional condensing device (K2), and a second condensing device (K4). When K2 is not present, first condensed liquid medium is diverted directly to the stripper unit (K3).

Figure 5:
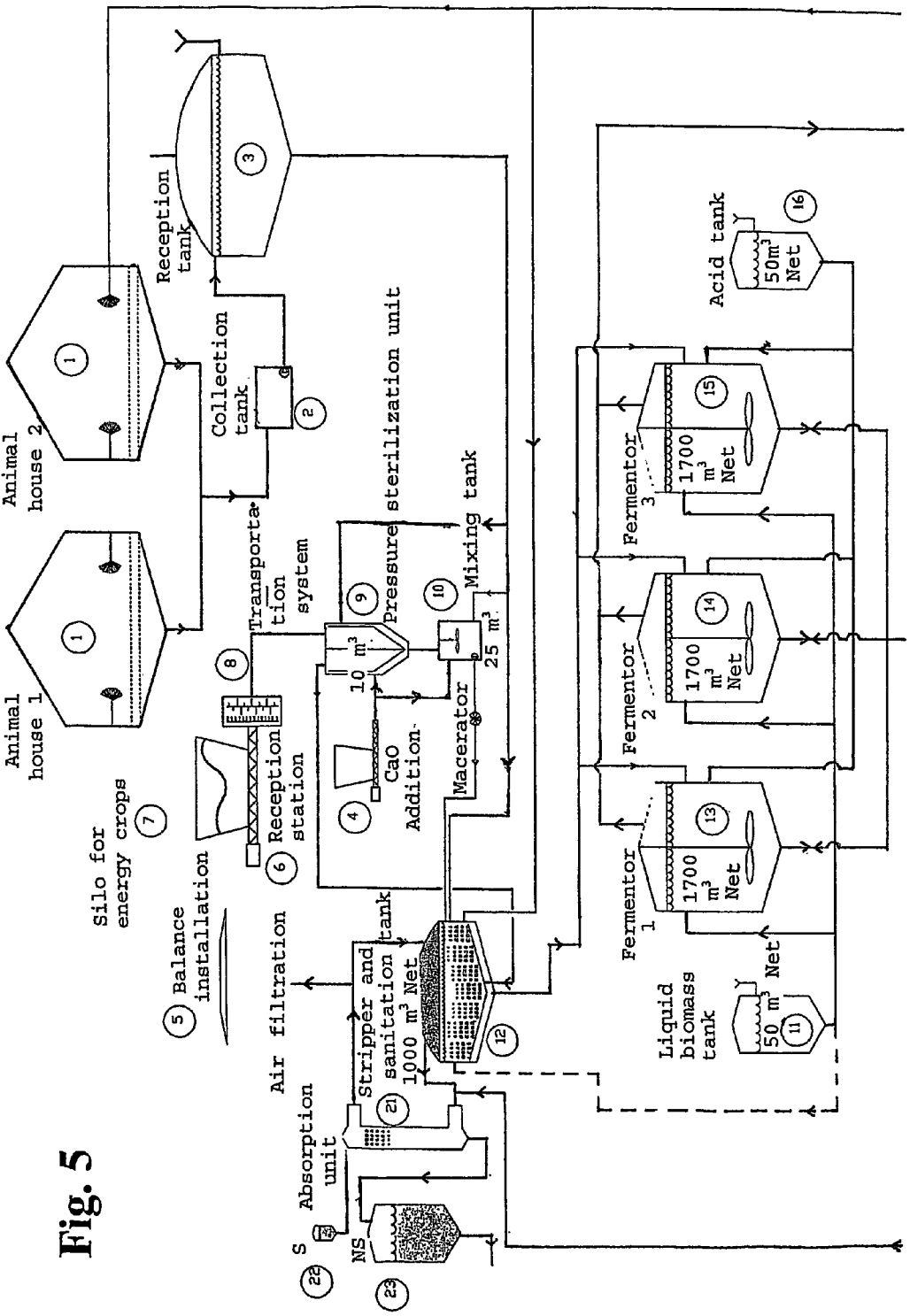
Figure 6:
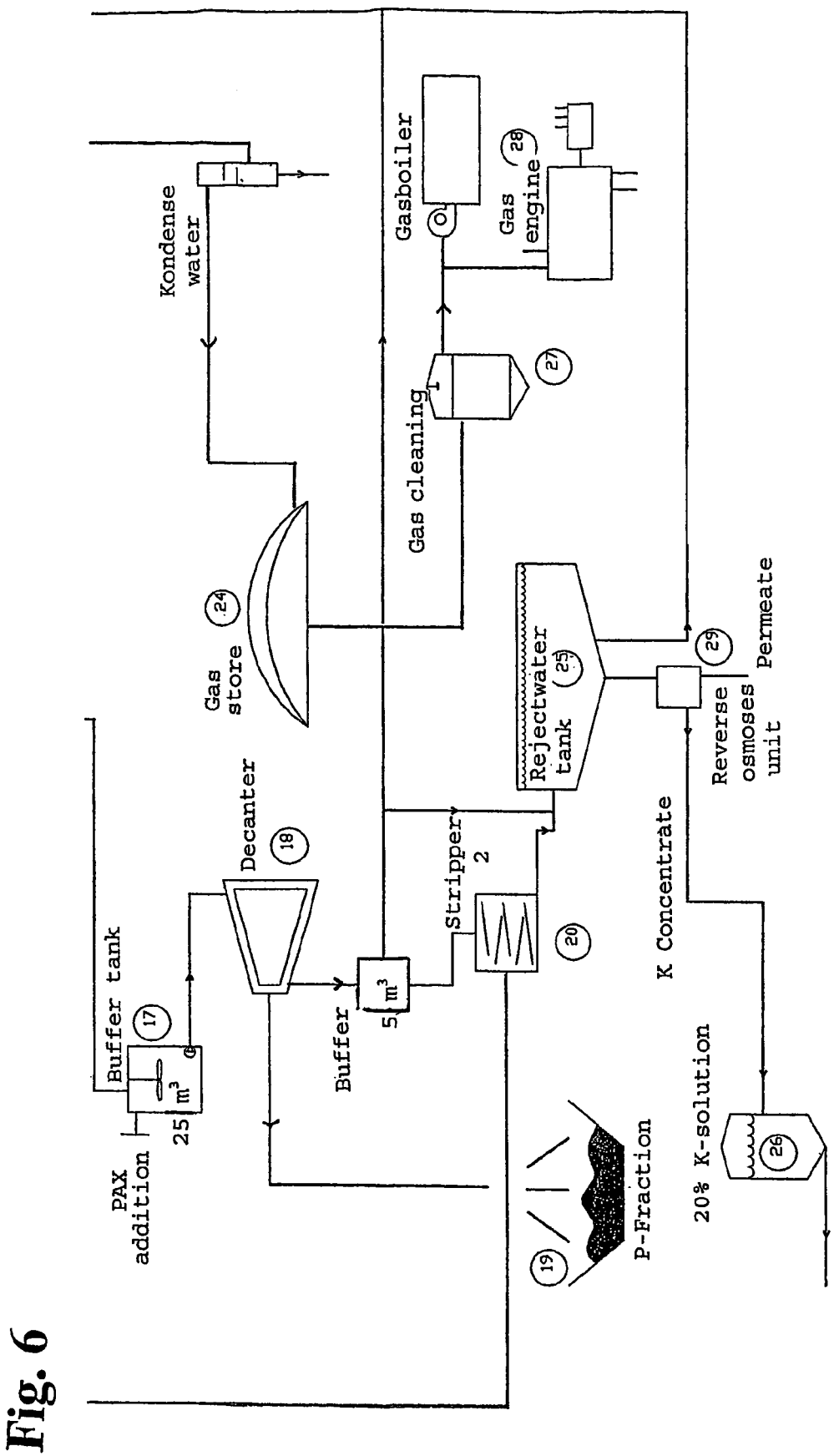

FIGS. 5 and 6 in combination illustrate the units of another plant for processing organic material. Also in this case is it possible to integrate the shunt, the stripper unit and associated condensing device(s) of the present invention with one or more fermentors or biogas reactor(s) forming part of a plant for processing organic material.

FIG. 7 is an illustration of a flow diagram depicting a simplification of the shunt and the connected processing plant according to the invention and processes relating thereto.

DETAILED DESCRIPTION OF THE INVENTION

The below sections disclose in more detail preferred embodiments of the present invention relating to a system comprising a shunt and stripper device(s) for stripping volatile compounds such as e.g. ammonia from a liquid comprising such volatile compounds. The system and/or the methods of the present invention can be used to:

eliminate or reduce the emission to the environment of dust, microbial organisms, ammonia, contaminated air, liquid or any other constitution within the system, especially from animal houses. This would require integration of the invention with a system comprising animal houses, biogas and nutrient refinement.

improve the utilisation of the energy contained in a biomass including organic material.

improve the production of biogas comprising methane gas and methane-bearing gas. Said gas may be stored in a tank locally and/or can be diverted to a commercial net of distributing gas and/or be incinerated in a gas motorgenerator to produce electricity and heat.

obtain separate fractions of N (nitrogen), P (phosphor) and potentially K (potassium) from organic materials. Said fractions are of commercial value and can be utilised as fertilisers to fertilise agricultural and horticultural crops. The separate fractions of P and K can be isolated from the remains from the organic materials subjected to anaerobic fermentation. The remains in the form of a slurry comprising solids and liquids are preferably diverted to at least decanter centrifuge for separating solids and fluids. One result of this separation is an at least semi-solid fraction preferably comprising almost exclusively P (phosphor), or an at least semi-solid fraction preferably comprising from 2 to 10% (w/w) P. In the same step, or in another decanter centrifuge separation step, a liquid fraction preferably comprising almost exclusively K (potassium), or a liquid fraction preferably comprising about 5 to 15% (w/w) K can preferably also be obtained. These fractions, preferably in the form of granulates obtained after a drying step, including a spray drying step or a slurry drying step, comprise P and/or K in commercially acceptable purities readily usable for commercial fertilisers. Such fertilisers may be spread onto crops or agricultural fields. The liquids resulting from decanter centrifuge separation step(s), such as reject water, can also be diverted to agricultural fields, they can be diverted back to e.g. a stable or animal house, or into a sewage treatment system.

obtain an improved animal welfare and improved hygiene in animal stables and in accordance to output from said animal stables. Said output comprising manure, slurry and animals to be slaughtered. The clean animals reduces the risk of infection of meat when the animals are slaughtered. The processing of the animal waste by means of the invention in biogas and nutrient refinement plants also reduces the risk of spreading viral and microbial organisms and pathogens to the environment.

obtain a procedure for rendering animal carcases or fractions hereof, meat and bone meal or any other produce from animals available for disposing off to agricultural land in the form of refined fertilizers and thus to benefit from micro- and macro-nutrients in the animal produce in the agricultural or horticultural plant production.

Working Principle of the Invention

Anaerobic microorganisms are obligate anaerobic and conventional ammonia stripping systems using e.g. atmospheric air is therefore not possible. Stripping with inert gasses is not very efficient or economically feasible. Likewise, it is not acceptable to apply conventional steam stripping because the temperature would kill off the important microbial organisms. The solution provided by the invention is therefore based on cold steam and vacuum because the microorganisms are tolerant to even very low pressures.

One step of the process step of the invention involves a first condensing device (K1). This step generates a first condensed aqueous liquid and a vapor not condensed by the first condensing device. The first condensing device operates at a low pressure below said predetermined reference pressure, preferably a reference pressure of 1 bar. Vapor not condensed by the first condensing device is optionally diverted in a further process step to a further condensing device (K2) at a pressure below the predetermined reference pressure. The objective is to remove a substantial part of the remaining volatile compounds such as e.g. ammonia from said vapor not condensed by the first condensing device. The objective is achieved by including a washing step using a counter current of aqueous liquid, obtaining an aqueous liquid fraction comprising volatile compounds such as e.g. ammonia and optionally vapor not condensed by the further condensing device.

A further process step comprises diverting said first condensed aqueous liquid from K1, and optionally also said aqueous liquid fraction from K2, comprising volatile compounds such as e.g. ammonia from the first condensing device, and optionally also from the further condensing device, respectively, to said stripper unit (K3), where said condensate(s) are stripped of the volatile compounds such as e.g. ammonia by heating at a second pressure which is higher than the first pressure, preferably a pressure of 1 bar or more, and obtaining a hot volatile compound such as e.g. ammonia-comprising steam and aqueous liquid stripped off a substantial part of the volatile compounds such as e.g. ammonia.

The higher second pressure is obtained by heating the liquid medium comprising the aqueous liquid fraction from K2 comprising volatile compounds such as e.g. ammonia and/or the first condensed aqueous liquid medium from K1 comprising volatile compounds such as e.g. ammonia in the stripper unit K3 to a temperature of more than 100° C., such as more than 105° C., for example more than 110° C., such as more than 115° C., for example more than 120° C., such as more than 125° C., for example more than 130° C., such as more than 135° C., for example more than 140° C., such as more than 145° C., for example more than 150° C., such as more than 155° C., for example more than 160° C., such as more than 165° C., for example more than 170° C., such as more than 175° C., for example more than 180° C., such as more than 190° C., for example more than 200° C., and preferably less than 250° C.

In a preferred embodiment, a volume of bioreactor liquid comprising active biomass from the bioreactor is pumped to the shunt (S) as mentioned herein above, where cold steam at a temperature of from about 50° C. to about 65° C., such as from about 55° C. to about 65° C., for example from about 60° C. to about 65° C., such as from about 50° C. to about 60° C., for example from about 50° C. to about 55° C., such as from about 55° C. to about 60° C., for example from about 57° C. to about 62° C., such as about 60° C., is diverted to the shunt held under a vacuum of from about 0.05 to about 0.4 bar, for example from about 0.1 bar to about 0.4 bar, such as from about 0.15 bar to about 0.4 bar, for example from about 0.2 bar to about 0.4 bar, such as from about 0.25 bar to about 0.4 bar, for example from about 0.30 bar to about 0.4 bar, such as from about 0.35 bar to about 0.4 bar, for example from about 0.05 bar to about 0.35 bar, such as from about 0.05 bar to about 0.3 bar, for example from about 0.05 bar to about 0.25 bar, such as from about 0.05 bar to about 0.2 bar, for example from about 0.05 bar to about 0.15 bar, such as from about 0.05 bar to about 0.1 bar, for example from about 0.1 bar to about 0.15 bar, such as from about 0.15 bar to about 0.2 bar, for example from about 0.2 bar to about 0.25 bar, such as from about 0.25 bar to about 0.3 bar, for example from about 0.3 bar to about 0.35 bar, such as from about 0.35 bar to about 0.4 bar, depending on the running temperature of the bioreactor.

The cold steam obtained in the evaporator (E) is directed through the liquid medium comprising the active biomass in the shunt (S), which is equiped with diffusers. While contacting the reactor liquid comprising a biomass, the steam strips off volatile compounds such as e.g. ammonia.

The generated vapor/steam comprising volatile compounds such as e.g. ammonia preferably comprises about 1-10% volatile compounds such as e.g. ammonia, such as 2-10% volatile compounds such as e.g. ammonia, for example 3-10% volatile compounds such as e.g. ammonia, such as 4-10% volatile compounds such as e.g. ammonia, for example 5-10% volatile compounds such as e.g. ammonia, such as 5-9% volatile compounds such as e.g. ammonia, for example 5-8% volatile compounds such as e.g. ammonia, such as 5-7% volatile compounds such as e.g. ammonia, such as 6-10% volatile compounds such as e.g. ammonia, for example 7-10% volatile compounds such as e.g. ammonia, such as 8-10% volatile compounds such as e.g. ammonia, for example 9-10% volatile compounds such as e.g. ammonia, such as 1-9% volatile compounds such as e.g. ammonia, for example 1-8% volatile compounds such as e.g. ammonia, such as 1-7% volatile compounds such as e.g. ammonia, for example 1-6% volatile compounds such as e.g. ammonia, such as 1-5% volatile compounds such as e.g. ammonia, for example 1-4% volatile compounds such as e.g. ammonia, such as 1-3% volatile compounds such as e.g. ammonia, for example 1-2% volatile compounds such as e.g. ammonia, such as 2-4% volatile compounds such as e.g. ammonia, for example 4-6% volatile compounds such as e.g. ammonia, such as 6-8% volatile compounds such as e.g. ammonia, for example 8-10% volatile compounds such as e.g. ammonia, such as 2-3% volatile compounds such as e.g. ammonia, for example 3-4% volatile compounds such as e.g. ammonia, such as 4-5% volatile compounds such as e.g. ammonia, for example 5-6% volatile compounds such as e.g. ammonia, such as 6-7% volatile compounds such as e.g. ammonia, for example 7-8% volatile compounds such as e.g. ammonia, such as 8-9% volatile compounds such as e.g. ammonia, and this steam is subsequently condensed at a low, first pressure (in K1) and further concentrated (stripped) at higher second pressure (in K3) to achieve preferably a solution of as much as 25% volatile compounds such as e.g. ammonia in aqueous liquid, such as for example 22% volatile compounds such as e.g. ammonia in aqueous liquid, for example 20% volatile compounds such as e.g. ammonia in aqueous liquid, for example 18% volatile compounds such as e.g. ammonia in aqueous liquid, for example 16% volatile compounds such as e.g. ammonia in aqueous liquid, for example 14% volatile compounds such as e.g. ammonia in aqueous liquid, for example 12% volatile compounds such as e.g. ammonia in aqueous liquid, for example 10% volatile compounds such as e.g. ammonia in aqueous liquid, for example 8% volatile compounds such as e.g. ammonia in aqueous liquid, and preferably a solution of more than 5% volatile compounds such as e.g. ammonia in aqueous liquid.

The target concentration of e.g. ammonia in the biogas reactor is about 3 kg N per tonnes, or less, such as about 2.9 kg N per tonnes, for example 2.8 kg N per tonnes, such as about 2.7 kg N per tonnes, for example 2.6 kg N per tonnes such as about 2.5 kg N per tonnes, for example 2.4 kg N per tonnes such as about 2.3 kg N per tonnes, for example 2.2 kg N per tonnes, such as about 2.1 kg N per tonnes, for example 2.0 kg N per tonnes, such as about 1.9 kg N per tonnes, for example 1.8 kg N per tonnes, such as about 1.7 kg N per tonnes, for example 1.6 kg N per tonnes, such as about 1.5 kg N per tonnes.

This target concentration is set based on two considerations. Firstly, the ammonia inhibition is released even at running temperatures of 60° C. in the bioreactor. Secondly, it is energetically easier to strip the "upper" N from 3 kg to e.g. 1.5 kg N than a complete stripping to perhaps 10 ppm ammonia. This also leaves some N remaining in the bioreactor for the metabolism of the microorganisms.

Advantages Associated with the Invention

Using this invention a number of advantages are achieved:

1. The ammonia concentration of active bioreactors is controlled and the co-digestion of N-rich wastes such as N-containing animal bi-products, including meat and bone meal, with animal manures is rendered possible.

2. Ammonia is removed from the biomass and a pure N-fertiliser of commercial value is produced.

3. It has surprisingly turned out that by providing a two-step stripping process a relatively low amount of energy (steam) is necessary. As explained in detail herein above, a heating media of low value, such as waste heat, can be used to provide the cold steam. The first stripping step comprises stripping volatile compounds such as e.g. ammonia from the active biomass at reduced pressure (preferably e.g. 0.1 to 0.2 bar) below a predetermined reference pressure (preferably e.g. 1.0 to 2.5 bar, more preferably 1.0 bar), where the steam/volatile compounds such as e.g. ammonia steam (typically comprising about 4-6% ammonia) can subsequently be condensed at the said low pressure in a first condensing device (K1), and optionally also in a second condencing device (K2) condensing cold volative compound or ammonia steam not condensed in the first condensing device.

The second stripping step comprises stripping volatile compounds such as e.g. ammonia from said condensed liquid obtained from the first stripping step. The second stripping step is carried out by injecting hot aqueous steam into the stripper unit (K3), thereby generating a pressure at or above the pre-determined reference pressure in the stripper unit. The stripping ultimately results in condensing the hot steam comprising volatile compounds such as e.g. ammonia, thereby generating a condensate comprising as much as about 25% volatile compounds such as e.g. ammonia in an aqueous liquid solution.

The condensate obtained from the first stripping step (i.e. condensate obtained in K2) can preferably be diverted to a storage tank in which the pH of the condensate can be adjusted before the condensate is stripped for ammonia in the second stripping step. After pH adjustment the pH value of the condensate is preferably 9 or more, such as 9.5, for example 10.

4. The disclosed system also makes it possible to control the temperature in the biogas reactors. If the vacuum of the shunt is set somewhat lower than the vapor pressure of the active biomass, a net evaporation from the biomass will occur thus lowering the temperature of the active biomass (to be returned to the bioreactor). On the other hand, if the vacuum of the shunt is set somewhat higher than the vapor pressure of active biomass a net condensation will occur thus increasing the temperature of the biomass (to be returned to the bioreactor).

5. Low pressure (and thus cold steam as defined herein) provides the highest stripping efficiency per kg steam.

6. The invention provides an efficient and economical heat exchanger between warm wastewater or aqueous liquid and very inhomogeneous slurry or biomass. It is thus possible to replace mechanical plate heat exchangers, which are costly and difficult to manage due to scaling and fouling of heat exchange plates. Scaling results from precipitation of e.g. calcium carbonates or struvite, while fouling is often caused by adsorption of proteins to the plates.

If the process involves a heat exchanger between slurry in a slurry tank and wastewater or aqueous liquid, the pressure in the slurry tank is preferably higher than the vapor pressure of the slurry, but lower than the steam vapor in the steam generator. In this case the generated cold steam will effectively condensate in the slurry and thus release the heat to the slurry.

The wastewater or aqueous liquid for cold steam production can be untreated aqueous liquid comprising e.g. salts, suspended solids, dry matter etc. It is not necessary to clean the wastewater or aqueous liquid before steam production from the waste. The generated cold steam from e.g. such wastewater is directed through the liquid medium comprising volatile compounds such as e.g. ammonia within the shunt of the stripper device. The cold steam produced in e.g. an evaporator enters the shunt of the stripper device by diffusers located inside the shunt.

The heat exchangers of the system described herein above are cheap to manufacture and operate.

System Comprising a Stripper Device for Stripping Volatile Compounds

In a first preferred aspect of the invention there is provided a stripper device comprising a shunt and applications thereof for stripping ammonia as described herein.

Figure 1:
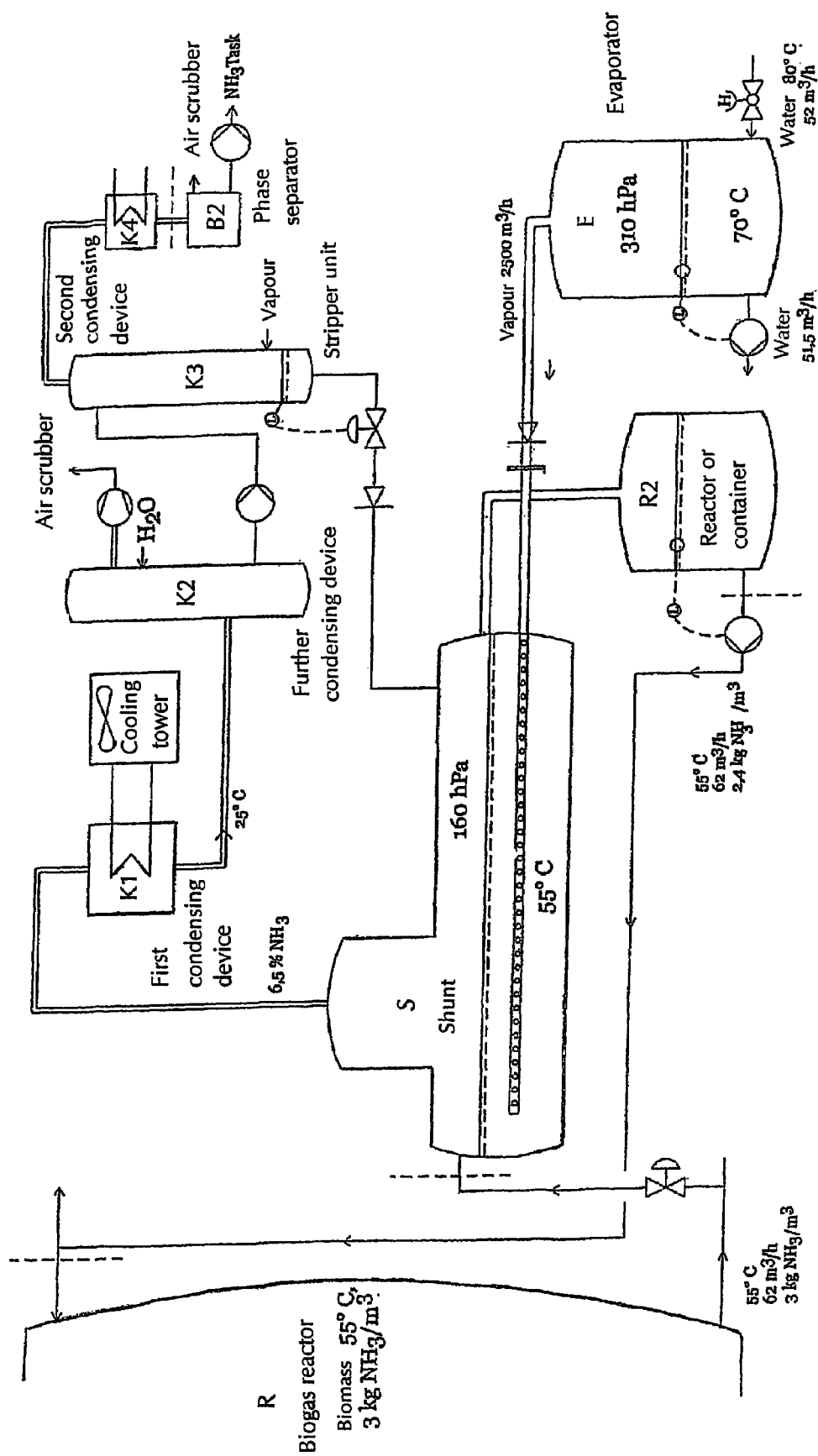

A side stream is diverted from an active bioreactor to the shunt where a substantial part of the ammonia content is removed before the side stream is diverted back to the bioreactor. This is illustrated in FIG. 1. The ammonia is removed to an extent, which allows the bioreactor to operate efficiently.

A second principal application is where the stripper device according to the present invention is used for an end-stripping purpose (such as e.g. illustrated in FIG. 6, component 2, "stripper 2"). In this application, a liquid such as e.g. reject water resulting from decanter centrifugation is purified from ammonia, i.e., it is stripped to very low concentrations of less than e.g. 200 ppm, such as less than 100 ppm, for example less than 50 ppm or even 10 ppm before the liquid is reused or disposed. In this case the liquid is preferably not shunted back to a bioreactor or any other process tank, but is simply purified to an extent, which allows reuse or final disposal of the liquid.

In the latter case a modified stripper unit is used where cold steam passes a column with course packed filter material over which the liquid is allowed to percolate in a counter current against the steam. This is necessary to achieve the stripping efficiency required to reach the low levels of ammonia, i.e., less than e.g. 50 ppm.

As an alternative to a column with course packed filter material one can apply a fluid bed column. One example of such a column is disclosed in U.S. Pat. No. 5,588,986 incorporated herein by reference.

Typically the stripping devide comprises a stripping column the characteristics of which has been designed according to methods known in the art, including but not limited to designs based on the commercial software design package Hyses™. Typically, it is preferred to use the stripping columns having 8-12 theoretical plates. A practical construction of such a stripping column, including design of column plates, inter-plate conduits, selection of column package materials etc., is known to a person skilled in the art. Commercial stripping columns are generally available from chemical engineering suppliers. The remaining components of the end-stripper application system are similar to the shunt application.

The stripper device K3 can be constructed to simulate a conventional stripper column where the stripping is performed by means of a counter current of steam against a current of percolation liquid.

However, it shall be designed to allow stripping of ammonia from a thick or viscous liquid with a high dry matter content of 10-50% typically between 10-20%, i.e. a typical liquid from an active bioreactor.

The column is prepared not by packing by filter material but is constructed with a number of horizontal plates with small holes and an opening for downward movement of the liquid from one plate to the following plate. The plates are placed at regular distances throughout the column.

The holes in the plates shall allow the cold steam to pass through the plates and the thick liquid thus striping off the ammonia. At the same time the steam shall keep the liquid and the dry matter in suspension so as to prevent settling of material on the plates.

The number of holes, plates and the amount of steam shall be adjusted to achieve the high stripping efficiency.

In a further aspect there is provided a system for reducing the concentration of volatile compounds in a liquid. Examples of volatile compounds include any compound capable of being stripped off a liquid media by vapor stripping/heating, optionally vapor stripping/heating under reduced pressure (i.e. below 1 bar), and subsequently collected by condensation of the vapor/steam generated as a result of the stripping/heating process. One example of a volatile compound is ammonia. Another example of volatile compounds is amines. Systems according to the invention can be designed for stripping off one or more volatile compounds present in a liquid medium. In one preferred embodiment the system is designed for stripping off ammonia from an aqueous liquid.

The systems according to the invention comprise technical features necessary for carrying out the methods of the invention as disclosed herein.

In one embodiment there is provided a system comprising a stripper device, said stripper device comprising a) a shunt (S) for stripping off volatile compounds from a liquid medium, wherein the shunted liquid medium is in liquid contact with a processing plant such as e.g. fermentor or a biogas reactor, b) a heat source, e.g. warm aqueous liquid, diverted to an evaporator (E), for producing cold steam to be diverted to the shunt (S), c) at least one condensing device (K1 and optionally K2) for condensing—preferably at a pressure below 1 bar—volatile compounds stripped off the liquid medium comprised in the shunt (S), d) a stripper unit (K3) for stripping by injection of hot steam—preferably stripping at a pressure at or above 1 bar—volatile compounds from a condensate generated by said at least one condensing device, and e) optionally a second condensing device (K4) for condensing volatile compounds stripped from the stripper unit, and f) valves, pipes and, when required, pumps for connecting the shunt to the heating source, to the condensing device(s) and to the stripper unit.

The condensates obtained with the present invention are obtained as a result of cooling of vapor/steam and not by compression.

The shunt preferably comprises an entry compartment in the form of a pre-degassing unit capable of regulating the composition of the cold steam being diverted to the condensing device(s). The bio-mass enters the pre-degassing unit via a plurality of spray nozzles capable of distributing the biomass to the surfaces of the splash plates.

It is preferred that primarily ammonia is diverted to the condensing device(s). Accordingly, the degassing unit preferably diverts gasses such as methane, carbondioxide and hydrogendisulphide to an air scrubber while ammonia is diverted from the pre-degassing unit to the shunt. Methane comprising gas can subsequently be diverted to a gasmotor in order to produce electricity and heating.

The pressure in the degassing unit depends on the temperature of the organic material being diverted to the pre-degassing unit. For a given temperature, the pressure in the pre-degassing unit will be higher than the pressure at which water boils at the temperature selected. Typically the pressure will be in the range of from 0.15 to 0.30 bar. The temperature in the pre-degassing unit will be above the boiling point of saturated aqueous vapor at the pressure in question.

The reason for the selection of a pressure higher than the pressure at which water boils at a given temperature is in order to prevent water and ammonia from evaporating in the pre-degassing unit. Also, the pressure must be sufficiently high so as to retain bicarbonate in the liquid phase. The retention of bicarbonate reduces the amount of carbondioxide produced.

The pressure in the pre-degassing unit is preferably provided by a liquid ring pump or a capsule blower. The pre-degassing unit preferably comprises splash plates to ensure a sufficient exposure of the liquids so that the gasses can be generated.

The volume of the pre-degassing unit shall be sufficient to ensure that the gasses can be generated and extracted within a suitable time, preferably less than about 10 seconds.

From the pre-degassing unit, the liquid bio-mass enters the shunt by means of a disc flow pump or an eccentric pump. Alternatively, vacuum can be used for transferring the liquid bio-mass from the pre-degassing unit and into the shunt compartment.

The cold steam from the evaporator can be diverted directly to the shunt or to the biomass entering the shunt.

One example of flow conditions and cold steam injection is:

| Input parameters: | |
| --- | --- |
| Biomass flow | 60 m$^3$ per hour |
| Temperature | 55° C. |
| Ammonia content | 3 kg per m$^3$ |
| Steam flow | 5.000 m$^3$ per hour |

(in one example 4.000 m$^3$ per hour from cold steam addition to the shunt, 1.000 m$^3$ per hour from cold steam being used for cooling the biomass)

Output Parameter:
Ammonia removal, up to 75 kg/hour,
Production of steam comprising an ammonia concentration of from 0,5 to about 5% ammonia.

Parameters for Stripper Unit (K3):
Steam flow 300 kg/hour at 2,5 bar at a temperature above 100° C. (e.g. 140° C.).

Output Parameter:
75 kg ammonia/hour as a condensate of up to approx. 25% ammonia.

The system according to the invention comprising the stripper device can further comprise a fermentor or a biogas reactor in liquid contact with the shunt as well as a container for collecting the stripped off and condensed volatile compounds.

Additionally, the system can comprise a pre-treatment plant. Substrates are processed in the pre-treatment plant prior to entering e.g. the fermentor or the biogas reactor. Examples of pre-treatment plants can include any one or more of the below:

a first pre-treatment tank, preferably a stripper tank for i) stripping N (nitrogen), including ammonia, from organic material, or ii) stripping N, including ammonia, from organic material collected from an additional pre-treatment tank, wherein this first pre-treatment tank can be used for hydrolysing the organic material, and/or a pre-treatment tank in the form of a lime pressure cooker for hydrolysing slurry comprising organic material, wherein said hydrolysis results in rendering the organic material available to microbial digestion in a bioreactor. It also eliminates, inactivates and/or reduces in number any viral or microbial organism and/or pathogenic organism present in the slurry, or a part thereof, and/or a pre-treatment tank in the form of a silage store for generating ensiled plant material comprising at least one or more of corn/maize, energy crops, beets, and any crop residues, and/or a pre-treatment fermentation tank for fermenting silage and/or lime pressure cooked organic material, in which the fermentation conditions are selected from mesophilic fermentation conditions and/or thermophilic fermentation conditions.

The processing plant preferably comprises a pressure sterilization unit, a stripper and sanitation tank, and one or more fermentors for biogas production.

The system of the invention is capable of processing organic material and obtaining the advantages described herein elsewhere. The system enables methods wherein the organic material can initially be subjected to one or more pre-treatments as listed herein above, followed by the formation of biogas by fermentation of said pre-treated organic material at mesophile and/or thermophile conditions as described herein while continuously removing volatile compounds such as e.g. ammonia from said fermentation liquid. The removal of ammonia involves initially using a shunt and an evaporator producing cold steam. Following condensation of cold steam comprising ammonia, the ammonia is stripped off the condensed liquid in a stripper unit. This generates a concentrated ammonia solution useful as a fertiliser. Following the above-mentioned fermentation, additional nutrient sources such as e.g. P (phosphor) and K (potassium) can be separated and isolated in individual fractions also useful as fertilisers.

The at least one condensing device for condensing cold steam as described herein can include two condensing devices, three condensing devices, four condensing devices, and more than four condensing devises. In one embodiment the system comprises two condensing devices. A condensation of cold steam comprising volatile compounds takes place in a first condensing device at a pressure below 1 bar, and a condensation of hot steam comprising volatile compounds such as e.g. ammonia takes place in a second condensing device at a pressure of 1 bar or more.

Vapor not condensed in the first condensing device K1 at the reduced pressure can optionally be diverted to a further condensing K2 device for condensation by washing in a liquid counter current. The condensed volatile compounds generated by condensation in the further condensing device K2 can subsequently be diverted to the stripper unit K3 e.g. together with first condensed aqueous liquid generated by condensation in said first condensing device K1. Vapor not condensed in the further condensing device can optionally be diverted to an air scrubber.

In one embodiment there is provided a system comprising a stripper device for stripping volatile compounds from a liquid medium, said stripper device comprising:

a) a shunt to which aqueous liquid medium comprising volatile compounds can be diverted in the form of a side stream to a fermentor or biogas reactor, b) pumps, valves and pipes for diverting aqueous liquid medium comprising volatile compounds to the shunt from said fermentor or biogas reactor, and c) an evaporator device comprising a sample of aqueous liquid to which heat obtained from an external heat source can be added, wherein a reduction of the pressure in said evaporator to a first pressure below a predetermined reference pressure generates cold steam, and d) pumps, valves and pipes for directing the cold steam generated by the evaporator of step c) through said aqueous liquid medium comprising volatile compounds in the shunt of the stripper device at said pressure below a predetermined reference pressure, thereby stripping off volatile compounds and obtaining a cold, volatile compound-comprising steam, and e) a first condensing device, and f) pumps, valves and pipes for diverting said cold volatile compound-comprising steam at said pressure below the predetermined reference pressure to the first condensing device, and condensing in a first condensing step in said first condensing device said cold volatile compound-comprising steam at said pressure below a predetermined reference pressure, thereby obtaining a first condensed aqueous liquid medium comprising said volatile compounds and vapor not condensed by the first condensing device, and, g) a stripper unit for stripping volatile compounds at said predetermined reference pressure or at a second pressure higher than said predetermined reference pressure, h) pumps, valves and pipes for diverting said first condensed aqueous liquid medium comprising volatile compounds obtained in step f) to the stripper unit, and stripping off at least part of the volatile compounds from said first condensed aqueous liquid medium comprising volatile compounds by injecting hot aqueous steam at said reference pressure or at the higher second pressure, thereby obtaining a hot volatile compound-comprising steam and aqueous liquid stripped off at least part of said volatile compounds, i) a second condensing device, and pumps, valves and pipes for diverting said hot volatile compound-comprising steam to a second condensing device, and condensing said hot volatile compound-comprising steam, thereby obtaining a condensate comprising volatile compounds.

In another embodiment the system comprising the stripper device for stripping volatile compounds comprises:

a) a shunt S to which aqueous liquid medium comprising volatile compounds can be diverted or shunted in the form of a side stream, b) pumps, valves and pipes for diverting aqueous liquid medium comprising volatile compounds such as e.g. ammonia to the shunt, and c) an evaporator device E for producing steam from a sample of warm aqueous liquid diverted to the evaporator by reducing the pressure below a predetermined reference pressure, and d) pumps, valves and pipes for directing a cold steam generated by the evaporator E of step c) through said liquid medium comprising volatile compounds in the shunt S of the stripper device by said pressure below a predetermined reference pressure, thereby stripping off volatile compounds and obtaining a cold, volatile compound-comprising steam, and e) a first condensing device and a second condensing device, and optionally a further condensing device, f) pumps, valves and pipes for diverting said cold volatile compound-comprising steam at said pressure below a predetermined reference pressure to the first condensing device, and condensing in a first condensing step in said first condensing device said cold volatile compound-comprising steam by said pressure below a predetermined reference pressure, thereby obtaining a first condensed aqueous liquid medium comprising said volatile compounds and vapor not condensed by the first condensing device, and g) optionally pumps, valves and pipes for diverting said vapor not condensed by the first condensing device to the further condensing device, when present, and removing a substantial part of the remaining volatile compounds from said vapor not condensed by the first condensing device, said removal involving washing the vapor in a counter current of aqueous liquid, thereby obtaining an aqueous liquid fraction comprising volatile compounds and vapor not condensed by the further condensing device, and h) pumps, valves and pipes for diverting said first condensed aqueous liquid medium comprising volatile compounds obtained in step f) and optionally also said aqueous liquid fraction comprising volatile compounds obtained in step g) to a stripper unit, and stripping off the volatile compounds from said first condensed aqueous liquid medium comprising volatile compounds such as e.g. ammonia and optionally also from said aqueous liquid fraction comprising volatile compounds such as e.g. ammonia by heating at a higher second pressure, thereby obtaining a hot volatile compound-comprising steam and aqueous liquid stripped off volatile compounds, and i) pumps, valves and pipes for diverting said hot volatile compound-comprising steam to a second condensing device, and condensing said hot volatile compound-comprising steam, thereby obtaining a condensate of volatile compounds.

The term "aqueous liquid stripped off at least part of volatile compounds" as used herein above shall denote an aqueous liquid medium comprising a reduced concentration of said volatile compound as compared to the concentration of the volatile compound in the aqueous liquid medium initially diverted to the shunt. A reduced concentration shall denote a reduction of at least 2 fold, such as 3 fold, for example 4 fold, such as 5 fold, for example 6 fold, such as 7 fold, for example 8 fold, such as 9 fold, for example 10 fold, such as 15 fold, for example 20 fold, such as 25 fold, for example 40 fold, such as 60 fold, for example 80 fold, such as 100 fold, or even more.

When the volatile compound is ammonia, the second condensed aqueous liquid (obtained from condensation of the hot vapor generated by the end-stripper unit) preferably comprises less than 10000 ppm ammonia, such as e.g. 5000 ppm ammonia, for example 4000 ppm ammonia, such as e.g. 3000 ppm ammonia, for example 2000 ppm ammonia, such as e.g. 1000 ppm ammonia, for example 800 ppm ammonia, such as e.g. 700 ppm ammonia, for example 600 ppm ammonia, such as e.g. 500 ppm ammonia, for example 400 ppm ammonia, such as e.g. 300 ppm ammonia, for example 250 ppm ammonia, such as e.g. 200 ppm ammonia, for example 150 ppm ammonia, such as e.g. 100 ppm ammonia, for example 80 ppm ammonia, such as e.g. 70 ppm ammonia, for example 60 ppm ammonia, such as e.g. 50 ppm ammonia, for example 40 ppm ammonia, such as e.g. 30 ppm ammonia, for example less than 20 ppm ammonia, such as less than 10 ppm ammonia.

The term "volatile compound" is used to describe any compound capable of being stripped off an aqueous liquid by heating said liquid, preferably heating combined with a reduced pressure, e.g. a pressure below 1 bar. The volatile compounds can be e.g. ammonia and/or methane or methane carrying gas.

The flows and concentrations illustrated in the figures constitute one realistic example of operating conditions of the shunt when coupled to a biogas reactor.

The stripper device and its components are described in more detail below in relation to stripping off volatile compounds such as e.g. ammonia from aqueous liquids.

Part of the volatile compounds-such as e.g. ammonia comprised in the aqueous liquid is stripped from the liquid in a stripper system comprising a shunt as illustrated in the figures. The shunt can be connected to a plant comprising e.g. a fermentor and/or a biogas reactor. Any plant generating liquids comprising volatile compounds such as e.g. ammonia during the operation of the plant is within the scope of the present invention. Examples include, but is not limited to, fermentors, biogas reactors, and plants generating waste water from the production of e.g. fertilisers.

The working principle of this aspect of the invention is that a fraction of the active biomass in the process tank is diverted to the shunt where the inhibitory substance such as e.g. ammonia is removed. It is essential that the various microbial consortia are left unaffected by the treatment because the digestion shall continue when the biomass is subsequently returned to the bioreactor. A substantial killing of the slow growing methanogenic bacteria would be lethal to the biogas process.

The shunt thus controls the concentration of the inhibitory substance such as e.g. ammonia in the bioreactor at a level sub critical to the anaerobic digestion and the operation of the bioreactor in general.

Accordingly, one aspect of the invention is directed to a method for reducing the concentration of volatile compounds such as e.g. ammonia in a liquid by stripping off at least part of the volatile compounds from the liquid, said method comprising the steps of a) providing a liquid medium comprising volatile compounds, and b) diverting said liquid medium comprising volatile compounds to a shunt operationally linked to a steam and heating source such as an evaporator and a heat source, respectively, and a condensing device, c) obtaining cold steam in the evaporator by reducing the pressure of the heating source below a predetermined reference pressure, and d) directing said cold steam through said liquid medium comprising volatile compound in the shunt of the stripper device at said pressure below a predetermined reference pressure, thereby stripping off volatile compound and obtaining a cold volatile compound-comprising steam, and e) diverting said cold volatile compound-comprising steam at said pressure below a predetermined reference pressure to a first condensing device, and f) condensing in a first condensing step said cold volatile compound-comprising steam at said pressure below a predetermined reference pressure, thereby obtaining a first condensed aqueous liquid medium comprising volatile compound, and g) diverting said first condensed aqueous liquid medium comprising volatile compound to a stripper unit, and h) stripping off the volatile compounds from said first condensed aqueous liquid medium comprising volatile compounds by heating said first condensed aqueous liquid in said stripper unit at a higher second pressure, and i) obtaining a liquid with a reduced concentration of volatile compounds.

In this aspect the liquid medium comprising volatile compounds such as e.g. ammonia, and optionally also amines, can be any such liquid as described herein elsewhere. The aqueous liquid can be water or any aqueous solution suitable for being diverted e.g. to a biomass in a fermentor. The method can include the further step of diverting from the first condensing device condensed aqueous liquid medium comprising ammonia to a further condensing device as described herein below in more detail.

In yet another embodiment there is provided a system for stripping of ammonia from a liquid, said system comprising
an evaporator for heating a sample of liquid, preferable a sample of aqueous liquid at a pressure below a predetermined reference pressure, to obtain a cold steam at a temperature below the boiling temperature of said liquid, and a stripper device for stripping ammonia from a liquid medium comprising ammonia by diverting said cold steam through said liquid medium comprising ammonia at said pressure below a predetermined reference pressure, obtaining a cold ammonia-comprising steam, wherein said liquid medium comprising ammonia is preferably a liquid medium from a bioreactor, such as a bioreactor for treating organic waste, in particular a bioreactor for treating animal manure and/or plant parts and/or slaugtherhouse waste, including meat and bone meal, said stripper unit comprising a first condensing device for condensing said cold ammonia-comprising steam at said pressure below a predetermined reference pressure, obtaining a first condensed aqueous liquid medium comprising ammonia, and a stripper unit for stripping said first condensed aqueous liquid medium comprising ammonia for ammonia by heating at a higher second pressure.

The system can further comprise at least one vapor evacuation pumps for evacuating vapor for producing said pressure below a predetermined reference pressure, In yet another embodiment there is provided a stripper device comprising:

(A) a first stripping unit, said first unit comprising:
(a) a stripping container for producing a vapor of volatile components from the liquid at a reduced pressure below a predetermined reference pressure;
(b) a first condensing device for condensing said vapor of volatile components from said stripping container at said reduced pressure;
(c) a phase separator for separating said condensed volatile components and said vapor of volatile components from said first condenser into a condensed phase and a vapor phase at said reduced pressure; and
(d) at least one vapor evacuation pumps for evacuating said vapor for producing a reduced pressure below said reference pressure; said vapor evacuation pumps being positioned down stream said first condenser; and (B) a second stripping unit, said unit comprising:
(e) a second stripping container for producing a vapor of volatile components from said condensed phase at said predetermined reference pressure; and
(f) a second condensing device for condensing said vapor of volatile components at said predetermined reference pressure, whereby it is obtained that heating media of low-value can be used for heating of the volatile components in the vacuum stripping process.

Preferred embodiments of the present invention are disclosed herein below in more detail.

The stripper device can be operably linked to a processing plant such as a bioreactor and/or any pre-treatment plant as disclosed herein elsewhere.

Further, allowing a first condensation process for producing intermediate concentrations of said volatile components; simple cooling media can be used in the condenser for condensing the first stripped volatile components.

Also, since main stream vapor compressor can be avoided, simpler and less expensive vapor compressors can be used.

Generally, the reduced pressure in the system of first stripping column, first condenser, and phase separator, can be any suitable pressure ensuring that volatile components are kept in their respective phases at the prevailing pressures and temperatures.

However, it may be desirable to have different operating pressures at the different units.

In a preferred embodiment, said first condenser, said phase separator have a pressure at or above said reduced pressure whereby it is obtained that volatile products are removed in a higher concentration using less heat but which volatile products can still be condensed using cooling water.

Generally, the liquid to be treated contains dissolved gasses, which may evaporate at the reduced pressure. Removal of these gasses is necessary for maintaining the reduced pressure.

Consequently, in a preferred embodiment, said at least one vapor evacuation pumps is connected to said phase separator whereby it is obtained that dissolved gasses can be removed.

The vapor evacuation pumps can be any suitable pumps for pumping the gasses in question. Consequently, in a preferred embodiment, said at least one vapor evacuation pumps is a displacement vacuum pump whereby removal of gas using a relatively inexpensive energy compressor with low energy demand is obtained.

The stripping container can be any container suitable for containing the liquid and volatile components in question as well as for operating at the required temperature and pressure.

Consequently, in a preferred embodiment, said first stripping container comprises; a container, an inlet, a heating means, a vapor outlet, a residue outlet, and internals, e.g. loose and fixed packing materials and plate-providing means such as a strainer; said container, inlet, vapor outlet, residue outlet, and internals being adapted to operate at a reduced pressure below said reference pressure.

In a preferred embodiment, said reference pressure is atmospheric pressure whereby particular simple and readily available equipment, in particular the second stripping container can be applied.

A person skilled in the art can select means for transportation of liquids and gasses.

For transportation of liquids any suitable pump meeting the physical and chemical properties of the liquid to be treated can be used. Thus, a suitable liquid pump is typically adapted to function with respect to viscosity, temperature and pressure of the liquid. Also, corrosive properties of the liquid and content of solid particles affect the choice of a pump of suitable construction and material. Generally, suitable liquid pumps include centrifuges, plunger pumps and displacement pumps, e.g. rotating displacement pumps.

Specific liquid pumps are preferably centrifugal pumps.

For transportation of gases any suitable pump meeting the physical and chemical properties of the gasses to be treated can be used. Thus, a suitable gas pump is typically selected to function with respect to required pressure and capacity, but also with respect to temperature, purity, energy demand, price, and corrosion properties. Generally, suitable gas pumps include blowers, and compressors.

Gas pumps used for providing a reduced pressure include vacuum pumps such as plunger pumps, displacement pumps and rotation pumps.

Specific vacuum pumps comprise preferably rotary displacement pumps.

In a preferred embodiment, the system comprises means for production of a combustion gas for combustion in a combustion engine whereby it is obtained that any heat produced from the combustion gas as a low-valued cooling media can be used as heating medium.

In a preferred embodiment, the system comprises means f or converting heat produced by combustion of said combustion gas to produce a vapor of volatile components in a stripping container of said vapor stripping apparatus, in particular according to the invention.

Generally, liquid comprising volatile components can be treated according to the invention. However, it is desired that the liquid exhibits certain properties. Consequently, the liquid can have been subjected to various treatments before being entered into the first stripping container.

In a preferred embodiment relating to the treatment of liquids of manure, said treatment comprises wholly or partial hydrolysis, biological degassing, and mechanical separation of solid matter whereby it is obtained that the gas production (and in this way the energy production) is maximized, and that organic products which might harm the process are minimized.

The systems described herein above can further comprise a first phase separator operating at said pressure below a predetermined reference pressure, for separating said first condensed aqueous liquid medium comprising ammonia and vapor not condensed by the first condensing device.

The systems can comprise a further condensing device, whereto said vapor not condensed by the first condensing device is diverted at said pressure below a predetermined reference pressure, removing a substantial part of the remaining ammonia by washing in a counter current of aqueous liquid medium, and obtaining a aqueous liquid fraction comprising ammonia and vapor not condensed by the further condensing device.

The systems can also comprise a second condensing device condensing said hot ammonia-comprising steam by cooling, thus obtaining a second condensed aqueous liquid medium comprising ammonia.

The second condensing device is preferably two heat exchangers cooling said hot ammonia-comprising steam to generate said second condensed aqueous liquid medium comprising ammonia in two steps, thus directing the obtained heat to said evaporator to heat liquid in said evaporator. The heat exchangers can be connected to heating means outside of the system.

The system can further comprise a second phase separator for separating said second condensed aqueous liquid medium comprising ammonia and vapor not condensed by the condensing device.

The systems can further comprise at least one air scrubber for cleaning said vapor not condensed by the condensing device(s), as well as cooling tower(s) for cooling aqueous liquid by evaporation to the atmosphere, and preferably also a storage container for storing said second condensed aqueous liquid medium comprising ammonia.

The system can comprise conventional connecting means, such as pipes, tubes cylinders, pipelines, hoses, hosepipes, canals, and ducts, preferably for connecting or operationally linking any one or more of:

one or more bioreactor(s) with the stripper device, and connecting in the stripper device itself:
the evaporator with the shunt, and
the shunt with the first condensing device, and
the first condensing device with the cooling tower, and
the first condensing device with the first phase separator, and
the first phase separator with the further condensing device, and
the first phase separator with the stripper unit, and
the further condensing device with the air scrubber, and
the further condensing device with the stripper unit, and
the stripper unit with the second condensing device, and
the further condensing device with the evaporator, and
the further condensing device with a heat exchanger, and
the second condensing device with the second phase separator, and
the second condensing device with the evaporator, and
the second condensing device with the storage container, and
the heat exchangers with the evaporator, and
the heat exchangers with the cooling tower.

The pumps of the system are capable of pumping liquid medium or vapor through said connecting means.

Figure 2:
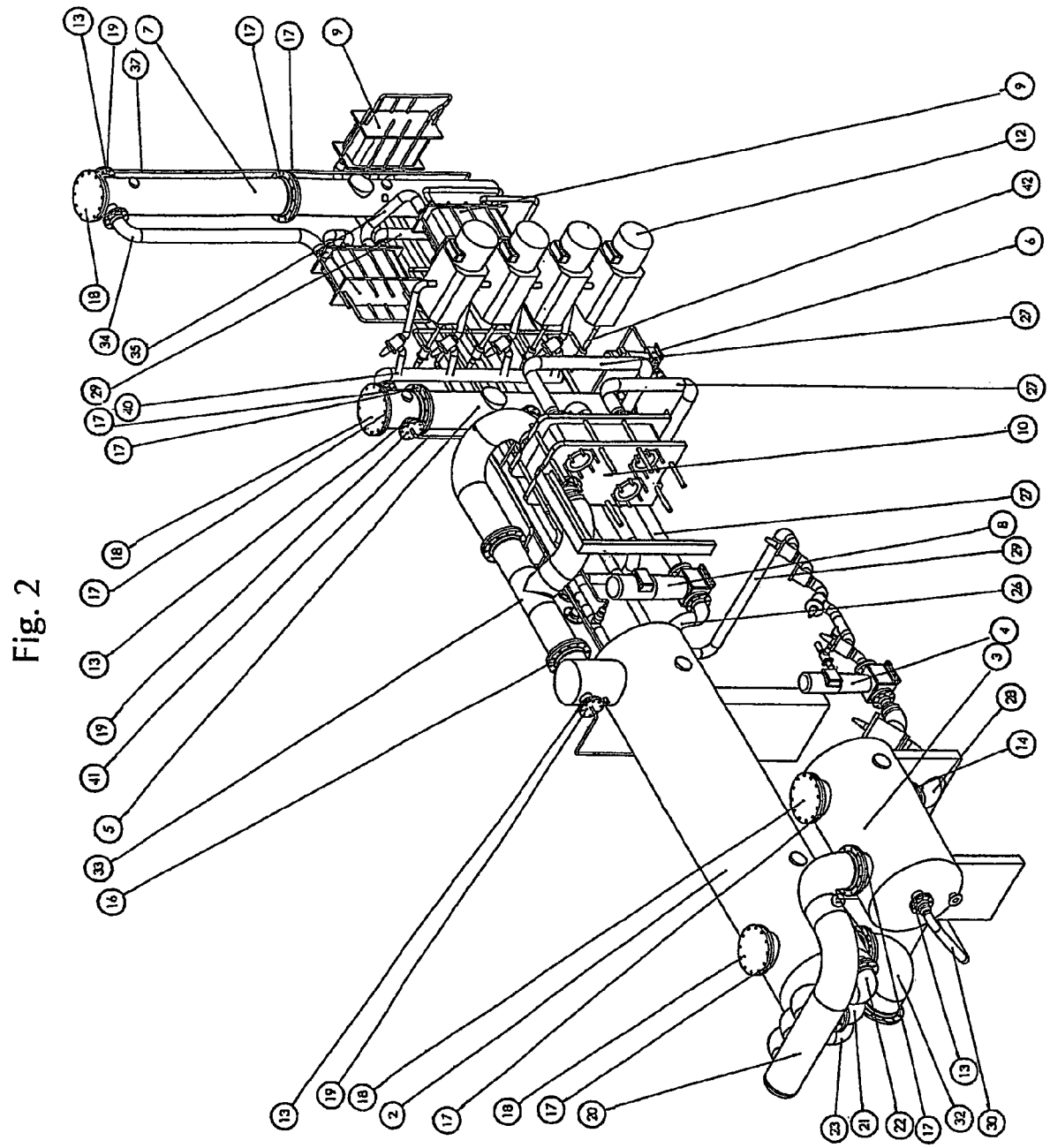
FIG. 2 illustrates another embodiment of the stripper device of the invention. In this embodiment, the invention is capable of being exploited as a mobile unit.

In another embodiment there is provided a mobile unit comprising a system for stripping ammonia from a liquid medium as described herein. The stripper device of the mobile unit is illustrated in FIG. 2.

Process Plants Linked to the Stripper Device

The following sections disclose specific embodiments of the invention wherein the aforementioned stripper device comprising a shunt and condensing device(s) is operationally connected to a processing plant for processing organic material. The organic material can comprise e.g. animal manure, such as pig and/or cow manure, and/or animal slurry, such as pig and/or cow slurry, and/or plant parts, wherein said plant parts comprise one or more of straw, crops, crop residues, silage, energy crops. Another example of material capable of being processed in connection with the present invention is animal carcasses or fractions hereof, slaughterhouse waste, meat and bone meal, blood plasma, and the like, originating from animals, as well as risk- and no-risk material with respect to the potential presence of BSE-prions or other prions.

After an optional pre-processing or pre.treatment depending on the kind of material used, said material is diverted to e.g. a biogas reactor wherein said organic material is fermented at mesophilic or thermophilic conditions, wherein said fermentation generates biogas.

The fermentor and/or biogas reactor can be further operably linked to additional units such as e.g. any one or more of a lime pressure cooker and a pre-treatment plant, as described in more detail herein below.

Fermenting organic material in a biogas fermentor can involve fermentation processes in one or more plants.

In one embodiment, the biogas production is performed in two plants by anaerobic bacterial fermentation of the organic material, initially by fermentation at thermophilic temperatures in a first plant, followed by diverting the thermophilicly fermented organic material to a second plant, wherein fermentation at mesophilic temperatures takes place.

The thermophilic reaction conditions preferably include a reaction temperature ranging from 45° C. to 75° C., such as a reaction temperature ranging from 55° C. to 65° C., such as about 60° C.

The mesophilic reaction conditions preferably include a reaction temperature ranging from 20° C. to 45° C., such as a reaction temperature ranging from 30° C. to 35° C. The thermophilic reaction as well as the mesophilic reaction is preferably performed for about 5 to 15 days, such as for about 7 to 10 days.

Any potential foam formation can be reduced and/or eliminated by the addition of polymers (polyglycols), silozanes, fatty acids, and/or plant oils, and/or one or more salts, preferably plant oil in the form of rape oil. The salts preferably comprise or essentially consist of CaO and/or $Ca(OH)_2$.

A desirable flocculation of substances and particles during biogas production is preferably achieved by the addition of calcium-ions capable of forming calcium-bridges between organic and inorganic substances in solution or suspension, wherein said calcium-bridges resulting in the formation of 'flocks' of particles. The addition of calcium-ions further results in the precipitation of orthophosphates, including dissolved ($PO_4^{3-}$), which is preferably precipitated as calcium phosphate $Ca_3(PO_4)_2$ wherein the precipitated calcium phosphate preferably remains suspended in a slurry.

The obtained biogas can be diverted to a gas engine capable of producing heat and/or electricity. The heat can be used to heat a lime pressure cooker and/or the fermentation plant and/or a N stripper reactor and/or the one or more biogas plant(s) and/or an animal house(s) and/or a human residence and/or heating aqueous liquid to be used in a household or human residence. The electricity can be diverted and sold to a commercial net for distributing electricity. In one preferred embodiment, the remaining N stripped, sterilised and fermented organic material is spread on agricultural fields.

Prior to fermentation in the biogas plants, the organic material can be treated in a lime pressure cooker. The lime pressure cooker of the system is preferably an apparatus, which is initially capable of cutting the organic material into segments and subsequently capable of diverting the segmented organic material to a chamber wherein said segmented organic material is heated and simultaneously exposed to a high pressure due to the elevated temperature. The organic material to be treated in the lime pressure cooker is added an amount of lime, including CaO and/or Ca(OH)$_2$ prior to or after entry into the lime pressure cooker.

Preferably CaO is added to the lime pressure cooker in an amount of from 25-100 g per kg dry matter in the organic material. The system operates at a temperature of between 100° C. and 220° C., such as e.g. 180° C. to 200° C. The temperature is aligned according to the organic material to be treated, a higher temperature is chosen the higher the content of cellulose, hemicellulose and lignin is in the organic material, or a higher temperature is chosen according to the risk of infectious microbial organism or pathogenic compounds including BSE prions in the organic material such as e.g. meat and bone meal.

The pressure in the lime pressure cooker is preferably between from 2 to preferably less than 16 bar, such as from 4 to preferably less than 16 bar, for example from 6 to preferably less than 16 bar, such as from 10 to preferably less than 16 bar. The system operates at the elevated temperature for about 5 to 10 minutes, but longer treatment times can also be used.

N including ammonia stripped in the lime pressure cooker is preferably collected and diverted to a column and absorbed as described herein elsewhere.

Prior to fermentation in the biogas plants, the organic material in the form of silage such as e.g. maize, energy crops, beets, and/or any crop residues, can be diverted to a mesophilic or thermophilic fermentation tank, before the material is further diverted to the stripper tank.

The lime pressure cooked organic material can also be diverted to a mesophilic or thermophilic fermentation tank, before the material is diverted to the stripper tank.

The invention also facilitates the optimization of the fermentation of the organic material and the production of biogas by providing a pre-treatment plant comprising facilities for stripping N including ammonia and/or performing alkaline hydrolysis under predetermined process parameters, including pH level, temperature, aeration, duration, foam inhibition and flocculation of suspended material.

In another embodiment of the invention the method ensures optimised conditions for the population of microbial organisms contained in the biogas producing fermenters. This is achieved by e.g. diverting sterilised or sanitised slurry from the stripper tank to at least a first biogas fermenter, wherein said sterilised or sanitised slurry do not inhibit or harm the population of biogas producing microbial consortia in the fermenter. In particular, organic material from which N including ammonia is stripped, can be diverted to a biogas reactor in which the fermentation conditions supports a mesophilic fermentation. Once the organic material has been subjected to a mesophilic fermentation, the organic material is preferably diverted to another biogas reactor of the system, in which the fermentation conditions are capable of supporting a thermophilic fermentation.

The organic material fermented in the biogas plants may also constitute organic material obtained from animal houses. In one embodiment the organic material from the animal houses is diverted to the stripper tank before fermentation in the biogas fermentors. The animal organic material is preferably from farm animals including cows, pigs, cattle, horses, goats, sheep and/or poultry, and the like. The organic material from animal houses may constitute solid and/or liquid parts selected from manures and slurries thereof, and animal carcasses or fractions thereof, such as e.g. meat and bone meal.

In the fermentation process in the biogas fermentors, the bacteria preferably produce mainly methane and a smaller fraction of carbon dioxide when fermenting the organic material. When the content of ammonia in the liquid in the biogas fermentor reaches a level above about 5 kg/m$^3$, the bacteria population is negatively affected to such a degree that the fermentation process is severely hampered. The influence of the ammonia can be controlled by using the present invention so that the ammonia level is kept below about 4 kg/m$^3$, such as a level of about 3 kg/m$^3$, or lower if desirable.

In an embodiment of the invention the ammonia content of the fermentation liquid of a biogas fermentor is lowered by stripping off part of the ammonia from the fermentation liquid in a shunt as described herein elsewhere in more detail, and the fermentation liquid stripped of part of the ammonia can subsequently be returned to the biogas fermentor.

In addition to the aforementioned pre-treatment plans the stripper device comprising the shunt, the condensing device (s) and the stripper unit, can also be operably connected to a pre-shunt degassing unit.

Biogas consists of methane and carbon dioxide. The biogas, which is produced within the active biomass, i.e., a slurry of micro-organisms, substrate, dissolved salts, nutrients, gasses etc. continuously escapes from the biomass slurry and is subsequently diverted to, e.g., a motor-generator unit.

The solubility of methane gas in water is of the order of $2 \times 10^{-5}$ expressed as mole fraction at a temperature of about 300K, while the solubility of carbon dioxide is of the order of $5 \times 10^{-4}$ at 300 K.

Hence, at the operating conditions of bioreactors and in case of sufficient stirring and hydraulic residence time only traces of the produced methane and carbon dioxide gas is dissolved in the slurry. However, it cannot be excluded that micro-bubbles are trapped or adsorbed in the slurry and some practical evidence suggest that of the order of 5-10% of the total produced biogas may be trapped in the biomass slurry.

It is important that this methane is removed from the slurry before it enters the shunt. If not, the methane gas would escape to the atmosphere, which is unwanted because it is a potent greenhouse gas and because it effectively reduces the biogas to be utilized in, e.g., the motor-generator plant. The presence of excess methane and carbon dioxide would also cause some difficulties to the stripping of ammonia and require higher vacuum capacity. If CO$_2$ were removed, on the other hand, the ammonia stripping would benefit from a slight pH increase according to the equations:

$$CO_2 + H_2O = H_2CO_3; \qquad \text{a)}$$

$$H_2CO_3 = H^+ + HCO_3^-; \qquad \text{b)}$$

$$HCO_3^- = H^+ + CO_3^{--}; \qquad \text{c)}$$

$$pH = pKa + \log\,[HCO_3^-]/[H_2CO_3], \qquad \text{d)}$$

from which appears, that removal of CO$_2$ or H$_2$CO$_3$ will shift the chemical equilibrium to the left resulting in consumption of H$^+$ ions. According to equation d) the normal concentrations of HCO$_3^-$ and H$_2$CO$_3$ are $25 \times 10^{-3}$ M and $1.25 \times 10^{-3}$ M at pH 7.4, which is a typical pH of biomass slurries.

In order to remove dissolved methane $CH_4$ (aq) and trapped methane $CH_4$ (g) from the biomass slurry it shall pass a pre-shunt degassing unit, which consists of a vacuum tank equipped with a disperser. Where the vacuum in the shunt is between 0.1-0.2 bars, the vacuum in the pre-shunt shall by between 0.6-0.8 bars. Such vacuum is sufficient to remove methane and carbon dioxide and will at the same time prevent ammonia from being stripped off the slurry in any significant quantities.

The methane and carbon dioxide is subsequently diverted to the motor-generator unit together with biogas from the bioreactors.

A number of organic substances in biomass slurry may cause foaming, which gives rise to operational difficulties of bioreactors etc. Lipids, proteins, fatty acids and extra cellular polymeric substances as well as filamentous microorganisms may cause foaming. In connection with high gas formation the risk of foaming is substantial. Thus, the ammonia stripping in the shunt (and also the stripping of other dissolved gasses) may stimulate foam formation.

However, if prone to foaming this will also occur in the pre-shunt degasser. This unit may therefore be equipped with a mechanical foam breaker such as a centrifuge or cyclone. In a cyclone the rotational force is superimposed on the centripetal force and foam entering a cyclone is therefore thrown at the wall under the influence of these forces, while the gas (methane and carbon dioxide) is forced into the centre of the cyclone and discharged through an outlet pipe (and, e.g., to a motor-generator plant). The condensed liquid phase may be circulated back in to the pre-shunt vessel or perhaps back into the bioreactor.

Introducing the pre-shunt degasser possibly equipped with a mechanical foam breaker thus substantially reduces the foaming potential of the biomass slurry and provides for an optimal performance of the shunt.

Chemical anti foaming agents may also be considered, however, these may interfere with the microbiological process in the bioreactor if not carefully selected.

Evaporator

The shunt of the stripper device is connected to a heating unit preferably in the form of an evaporator. In said evaporator aqueous liquid is heated to obtain warm aqueous liquid, where the heat is provided through an external source. Cold steam is produced by means of vacuum over the surface of the warm aqueous liquid, thus lowering the temperature of the liquid and thereby using the heat energy of the liquid.

In a preferred embodiment of the invention, the temperature of the aqueous liquid in the evaporator is about 60-80° C., such as 60-75° C., for example such as 60-70° C., such as 65-75° C., for example such as 65-80° C., such as 65-75° C., for example 68-72° C., such as about 70° C.

In another preferred embodiment of the invention, the pressure of the evaporator is about 200 to 500 hPa, such as about 200 to 450 hPa, for example about 200 to 400 hPa, such as about 200 to 380 hPa, for example about 250 to 380 hPa, such as about 250 to 370 hPa, for example about 250 to 360 hPa, such as about 270 to 360 hPa, for example about 270 to 350 hPa, such as about 270 to 340 hPa, for example about 270 to 330 hPa, such as about 270 to 320 hPa, for example about 280 to 320 hPa, such as about 290 to 320 hPa, for example about 300 to 320 hPa, such as about 310 hPa.

In a preferred embodiment the cold steam for the stripping process is produced by means of vacuum over a surface of warm aqueous liquid. This takes place in the evaporator. The temperature of the aqueous liquid in the evaporator is preferably maintained by means of e.g. cooling aqueous liquid from a motor-generator unit in a biogas plant, or alternatively, from any other waste heat source or motor-generator. The waste heat, in the form of warm aqueous liquid, can be present at temperatures as low as 60-70° C. Aqueous liquid at higher temperatures may also be used, however, in such cases the vapor has to be cooled to temperatures suitable to the microorganisms in the biogas reactor, i.e., at a maximum of 65° C. and preferably at a temperature close to the operating temperature of the bioreactor.

The system preferably comprises pipe lines constituting a closed system preventing or leading to a reduction in emissions of any one or more of dust, microbial organisms, ammonia, air, liquid or any other constituent within the system.

In a preferred embodiment said pressure below a predetermined reference pressure is obtained in the evaporator, the shunt, the first condensing device and the optional further condensing device.

In a further preferred embodiment said pressure below a predetermined reference pressure is preferably 0.1 to less than 1.0 bar, such as 0.1 to 0.4 bar, and more preferably from about 0.1 to about 0.35 bar.

In one preferred embodiment said pressure is about 0.27 bar to 0.35 bar, such as about 0.29 to about 0.33 bar, for example about 0.31 bar in the evaporator, and about 0.12 to about 0.20 bar, for example from about 0.14 to about 0.18, such as about 0.16 bar in the shunt, and from about 0.16 bar to about 0.24 bar, for example from about 0.18 bar to about 0.22 bar, such as about 0.20 bar in the first condensing device and in the optional further condensing device.

The aqueous liquid medium heated in the evaporator to produce said cold steam can be any aqueous liquid source preferably with a maximum ammonia concentration of 3 kg ammonia per tonnes of liquid, such as a maximum 2 kg ammonia per tonnes of liquid, for example a maximum 1 kg ammonia per tonnes of liquid, such as a maximum 0.5 kg or less ammonia per tonnes of liquid.

In a preferred embodiment said aqueous liquid source is tap water, waste aqueous liquid, or aqueous liquid from a biogas production.

The heating process in the evaporator is conducted by using heat exchangers reusing heat from machines, from warm waste aqueous liquid or from aqueous liquid of a cooling devices, such as from the first condensing device or from the second condensing device of a plant as described herein.

Condensing Device(s)

The present invention is disclosed herein below with respect to one or more condensing devices for condensing steam and vapors comprising volatile compounds including ammonia and volatile amines.

The condensing process steps can include the use of a first condensing device and optionally also a further condensing device for condensing cold steam comprising volatile compounds, and a second condensing device operationally linked to a stripper unit, wherein said second condensing device condenses steam comprising volatile compounds at a pressure at or above said reference pressure.

In one embodiment the invention provides for the generation of a vapor comprising volatile compounds including e.g. ammonia, which vapor is not condensed by the first condensing device, and said vapor not condensed by the first condensing device can subsequently be diverted to a further condensing device at said pressure below a predetermined reference pressure, removing at least a substantial part of the remaining ammonia as possible from said vapor not condensed by the first condensing device. This is possible by including a washing step exploiting a counter current of aqueous liquid, said washing step and said condensation resulting in an aqueous liquid fraction comprising ammonia and vapor not condensed by the further condensing device.

The aqueous liquid fraction comprising ammonia obtained from the further condensing device can be diverted to the stripper unit, where, together with the first condensed aqueous liquid medium comprising ammonia also diverted to said stripper unit, ammonia is stripped off by heating at said higher second pressure, and obtaining a hot ammonia-comprising steam and aqueous liquid stripped off at least part of said ammonia.

The hot ammonia-comprising steam obtained as described herein immediately above is diverted to a second condensing device capable of condensing said hot ammonia-comprising steam at or above said reference pressure, thereby obtaining a further condensed aqueous liquid medium comprising ammonia and optionally also vapor not condensed by the second condensing device.

The vapor not condensed by the further condensing device and/or the second condensing device can be directed to an air scrubber or released directly to the atmosphere.

The temperature of said first condensed aqueous liquid medium comprising ammonia is preferably 15-35° C., such as 20-30° C., for example 23-28° C., such as about 25° C.

The temperature of said counter current of aqueous liquid in the third condensing device is preferably 15-35° C., such as 20-30° C., for example 23-28° C., such as about 25° C.

The temperature of said first condensed aqueous liquid medium comprising ammonia and of said aqueous liquid fraction comprising ammonia in the stripper unit is preferably 80-170° C., such as 85-130° C., for example 90-110° C., such as about 100° C.

The temperature of said hot ammonia-comprising steam when leaving the stripper unit is preferably 50-110° C, such as 60-100° C, for example 70-90° C., such as about 80° C.

The temperature of said ammonia concentrate is preferably 15-45° C., such as 20-40° C., for example 25-35° C., such as about 30° C.

The aqueous liquid medium preferably comprises an amount of from 2.5 to 5 kg ammonia per m$^3$ (cubic meter), such as 2.6 to 4 kg ammonia per m$^3$, such as 2.7 to 3.5 kg ammonia per m$^3$, for example 2.8 to 3.2 kg ammonia per m$^3$, such as 2.9 to 3.1 kg ammonia per m$^3$, such as about 3.0 kg ammonia per m$^3$.

The liquid medium comprising ammonia is preferably liquid medium further comprising organic materials, preferably a liquid from a bioreactor, such as a bioreactor for treating organic waste, in particular a bioreactor for treating manure, including swine manure, and/or meat and bone meal.

The liquid medium comprising ammonia enters the shunt in one end, is diverted through the shunt simultaneously with the addition of cold steam, and the liquid medium subsequently leaves said shunt having a reduced concentration of ammonia.

The cold ammonia-comprising steam from the shunt preferably comprises ammonia in a concentration of about 0.5 to 10% ammonia, for example 0,5 to 8% ammonia, such as about 0.5 to 7% ammonia, for example about 0.5 to 6% ammonia, such as about 0.5 to 5% ammonia.

The second condensed aqueous liquid medium preferably comprises ammonia in a concentration of about 10-40%, such as 15-35%, for example such as 20-30%, such as about 25%.

The liquid with a reduced concentration of ammonia resulting from stripping off ammonia in the shunt preferably comprises ammonia in a concentration of less than 3 kg ammonia per tonnes of liquid, such as about 2.5 kg ammonia per tonnes of liquid, for example about 2.0 kg ammonia per tonnes of liquid, such as about 1.5 kg ammonia per tonnes of liquid, for example about 1.0 kg ammonia per tonnes of liquid, such as less than about 2.0 kg ammonia per tonnes of liquid, for example less than 1.0 kg kg ammonia per tonnes of liquid.

The liquid with a reduced concentration of ammonia is preferably shunted (back) to a bioreactor, such as to the bioreactor from where said liquid medium comprising ammonia was initially obtained, or to a bioreactor in connection with the bioreactor from where said liquid medium comprising ammonia was initially obtained.

It is important that the liquid having a reduced concentration of ammonia being diverted back to a bioreactor has no negative influence on the microorganisms in the bioreactor. It must not impair growth or enzyme activity of the microorganisms. The bioreactor is preferably mesophilic or thermophilic.

Biomasses of low and high contents of protein can be fermented in the bioreactor. Examples of biomasses with a high contents of protein can be animal bi-products e.g. meat and bone meal, vegetable protein, molasses and vinasse. The amount of meat and bone meal fermented in the bioreactor preferably comprises more than 2.5%, such as more than 5%, preferable more than 10%, such as more than 15%, such as more than 20%, such as more than 25% of the total biomass by weight. One use of the condensed aqueous liquid with a high ammonia concentration is for a commercial fertiliser.

The biomasses with high contents of protein, including meat and bone meal can be initially diverted to one or more pre-treatment plants before fermentation in said bioreactor, wherein said pre-treatment plants preferably comprises:

a first pre-treatment tank, preferably a stripper tank for stripping N (nitrogen), including ammonia, from the biomasses, and/or a second pre-treatment tank, preferably a lime pressure cooker for hydrolysing biomasses, wherein said hydrolysis results in eliminating, inactivating and/or reducing in number any viable microbial organisms and/or pathogenic substances present in the biomasses, or a part thereof, and/or at least one tank, preferably a silage store for generating ensiled plant material comprising at least one or more of corn/maize, energy crops, beets, and any crop residues, and/or at least one second tank, preferably a pre-treatment fermenting tank to ferment silage and/or lime pressure cooked organic material, in which the fermentation conditions are selected from mesophilic fermentation conditions and/or thermophilic fermentation conditions.

DETAILED DESCRIPTION OF THE DRAWINGS

FIG. 1 illustrates the main processes of one embodiment of the present invention.

R: R denotes a bioreactor, in this case a biogas reactor with an operating temperature of about 55° C. The ammonia concentration in the biogas reactor shall be held at a maximum of about 3 kg NH$_3$ per m$^3$.

S: The shunt S typically operates at a pressure below a predetermined reference pressure, preferable at a pressure below the atmospheric pressure. The liquid to be stripped for a fraction of its ammonia content is diverted from R to the S by means of a pump or inlet valve. During the passage of the liquid through the S, cold steam is directed through the liquid. The stripped liquid medium comprising liquid with a reduced concentration of ammonia is subsequently pumped back to the bioreactor R or to another bioreactor R2 in connection with the bioreactor R.

E: The cold steam for the stripping process is produced in the evaporator E by means of vacuum over a surface of warm aqueous liquid. The temperature of the aqueous liquid in the evaporator E is preferably maintained by means of e.g. cooling aqueous liquid from a motor-generator unit in a biogas plant, or alternatively, from any other waste heat source. The waste heat, in the form of warm aqueous liquid, can be present at temperatures as low as 60-70° C. Aqueous liquid at higher temperatures may also be used, however, in such cases the vapor has to be cooled to temperatures suitable to the microorganisms in the biogas reactor, i.e., at a maximum of 65° C. and preferably at a temperature close to the operating temperature of the bioreactor.

K1: In the shunt S, where cold steam is directed through the liquid and hereby removing at least part of its ammonia content, the produced mixture of steam and ammonia comprising cold ammonia-comprising steam is diverted from S to a first condensing device K1, where the cold ammonia-comprising steam is condensed to a first condensed aqueous liquid medium comprising ammonia which is a dilute ammonia/aqueous liquid solution by means of cooling aqueous liquid in a cooling tower.

K1 can be split in two parts (as can also K2 and K4) in order for the first part to produce relatively warm cooling aqueous liquid and the second part relatively cold cooling aqueous liquid. The relatively warm cooling aqueous liquid may in both cases be used directly in the shunt or any other heating purpose.

The cold cooling aqueous liquid from K1 and K4 having a temperature of 32° C. or somewhat less may be used in a heat pump to generate warm aqueous liquid at e.g. 60-70° C. for heating purposes. The energy factor per 1 kWh used in the heat pump will be around 4 because the cooling aqueous liquid is available at a stable temperature and at a stable flow. These are conditions, which favour the running of a heat pump.

K2: The vapor not condensed in K1 can optionally be diverted to the condensing device K2, where it is washed in a counter current of aqueous liquid in order to remove a substantial part of the remaining ammonia. The vapor remaining after the washing process can be diverted to a vacuum pump and further to a conventional air scrubber or directly to the atmosphere.

K3: The dilute ammonia/aqueous liquid solution produced in the K1 and optionally also K2 comprising the first condensed aqueous liquid medium comprising ammonia and the aqueous liquid fraction comprising ammonia is stripped for ammonia in the stripper unit K3 by means of hot steam at or above 100° C. and at a pressure above atmospheric pressure, i.e., at a higher second pressure (e.g. 2.5 bar) as compared to the lower first pressure (e.g. 0.16 bar) in S, K1 and optionally also K2.

K4: The concentrated ammonia/steam vapors from the stripper unit K3 comprising hot ammonia-comprising steam are condensed in the second condensing device K4 by means of cooling aqueous liquid in a cooling tower, preferably to a 25% ammonia/aqueous liquid solution.

B2: The second condensed aqueous liquid medium comprising ammonia and vapor not condensed by the second condensing device from K4 can be separated in the phase separator B2, and the second condensed aqueous liquid medium comprising ammonia is diverted to a storage tank and the vapor not condensed by the second condensing device is diverted e.g. to an air scrubber or directly to the atmosphere.

K1 and K4: Recycling of heat: The K1 and K4 cooling towers may both be split in two parts in order for the first part to generate relatively warm cooling aqueous liquid and in order for the second part to generate relatively cold cooling aqueous liquid at temperatures less than ambient temperature. The relatively warm cooling aqueous liquid may in both cases be used in the shunt or any other heating purpose. The cooling aqueous liquid generated in the first part of K1 will preferably have temperatures of about 40-45° C. whereas the cooling aqueous liquid from the first part of K4 will preferably have temperatures of 70-80° C. The cooling aqueous liquid from the second part of both K1 and K4 will be less than 25° C.

The cooling-aqueous liquid with temperatures of about 70-80° C. is well suited to be recycled to the evaporator E whereas the cooling aqueous liquid with temperatures of 40-45° C. may be used for any other heating purpose, e.g. preheating of cold biomass to be introduced into a biogas plant.

FIG. 2 illustrates one embodiment of the shunt and the end-stripper device. In this embodiment the shunt and the end-stripper device is capable of being used with a mobile unit such as a container.

The numbers in the below table refer to reference numerals in the figure.

| Item | Indication | Description |
|---|---|---|
| 1 | | Container |
| 2 | S | Shunt |
| 3 | E | Evaporator |
| 4 | | Pump between E and H6, H5, H3 |
| 5 | K2 | Further condensing device |
| 6 | | Pump between K1 and K2 |
| 7 | K3 | Stripper unit |
| 8 | | Pump |
| 9 | K4 | Second condensing device (Heat exchangers H3, H4, H5, H6) |
| 10 | K1 | First condensing device |
| 11 | | Cooling tower (not shown) |
| 12 | | Capsule vacuum blowers |
| 13 | | Pipe flange |
| 14 | | Pipe flange |
| 15 | | Pipe flange |
| 16 | | Pipe flange |
| 17 | | Pipe flange |
| 18 | | Blind flange |
| 19 | | Blind flange |
| 20 | | Pipe between E and S |
| 21 | | Manifold between E and S |
| 22 | | Manifold between E and S |
| 23 | | Manifold between E and S |
| 24 | | Pipe inlet between R and S |
| 25 | | Pipe between K1 and K2 |
| 26 | | Pipe to cooling tower |
| 27 | | Pipe between H2 and H4 |
| 28 | | Pipe between E and pump 6 |
| 29 | | Pipe between E, pump 6 and H6, H3 |
| 30 | | Pipe between E and H6, H3. |
| 31 | | Pipe between K2 and pump 7 |
| 32 | | Pipe from S to bioreactor R |
| 33 | | Pipe between S and K1 |
| 34 | | Pipe between H3 and K3 |
| 35 | | Pipe between H3 and H4 |
| 36 | | Pipe from H4 to an ammonia storage tank via a phase separator B2 |
| 37 | | Pipe between pump 7 and K3. |
| 38 | | Pipe between H6 and external supply of waste heat |
| 39 | | Pipe for return of cooled water between H6 and external heat source |
| 40 | | Vacuum manifold to K2 |
| 41 | | Water supply to S |

-continued

| Item | Indication | Description |
|---|---|---|
| 42 | | Exhaust vapor from vacuum blowers to air scrubber |

1. The container wherein the shunt is mounted to provide a separate unit, which can be integrated with a biochemical process plant. The container is not shown on the figure, but it preferably confines all but top of no. 5 and the upper part of no. 7.
2. The shunt S typically operates at a pressure below the atmospheric pressure. The liquid to be stripped for a part of its ammonia content is diverted from a bioreactor R to S by means of a pump or inlet valve. During the passage of the liquid through S, cold steam is directed through the liquid. The stripped liquid confining a liquid with a reduced concentration of ammonia is subsequently pumped back to the bioreactor R.
3. Evaporator E. The cold steam for the stripping process is produced by means of vacuum over a surface of warm aqueous liquid. This takes place in the evaporator E. The temperature of the aqueous liquid in the evaporator E is preferably maintained by means of e.g. cooling aqueous liquid from a motor-generator unit in a biogas plant, or alternatively, from any other waste heat source. The waste heat, in the form of warm aqueous liquid, can be present at temperatures as low as 60-70° C. Aqueous liquid at higher temperatures may also be used, however, in such cases the vapor has to be cooled to temperatures suitable to the microorganisms in the bioreactor. For a biogas reactor co-digesting animal manures with any other organic biomass the maximum temperature is 65° C. and the running temperature shall be close to the operating temperature of the biogas reactor, i.e. preferably between 55-60° C.
4. Pump P6, for pumping liquids and fluids between E and H6, H5, and H3.
5. Further condensing device K2.
6. Pump P7, to pump between K1 and K2.
7. K3 is a stripper unit for concentrating e.g. ammonia. The dilute ammonia/aqueous liquid solution produced in the K1 and optionally also K2 comprising the first condensed aqueous liquid medium comprising ammonia from K1 and the aqueous liquid phase comprising ammonia from K2 is stripped for ammonia in K3 by means of hot steam above 100° C. and at a pressure at or above atmospheric pressure, i.e., at a higher second pressure (e.g. 2.5 bar) as compared to the lower first pressure (e.g. 0.16 bar) in S, K1 and K2.
8. Pump P8, to pump circulating aqueous liquid for feed of heat exchanger K1 and K4.
9. Heat exchangers H3. H4. H5. H6. The H3 and H4 cool vapor from K3. The hot ammonia-comprising steam from K3 are condensed in the heat exchanger condensator H3 and H4 comprising the second condensing device K4. i.e., the condensation is spilt in two (H3 and H4) so as to re-circulate heat into the evaporator E. In H4 the remaining vapor from H3 are again condensed by means of cooling aqueous liquid in a cooling tower, to preferably a 25% ammonia/aqueous liquid solution. H5 cools a liquid from an external heat source, e.g., from a final stripping step in a complete biogas and refinement plant. H6 cools liquid from an external heat source, e.g. from a motor-generator plant fuelled by biogas from a complete biogas plant.
10. First condensing device K1. In the shunt S, where cold steam is directed through the liquid medium comprising ammonia and thereby removing a part of its ammonia content, the produced mixture of steam and ammonia constituting cold ammonia-comprising steam is diverted from the stripper device S to the first condensing device K1, where the cold ammonia-comprising steam is condensed to a dilute ammonia/aqueous liquid constituting the first condensed aqueous liquid medium comprising ammonia solution by means of cooling aqueous liquid in a cooling tower. The vapor not condensed in the K1 is optionally diverted to the further condensing device K2 where it is washed in a counter current of aqueous liquid in order to remove at least part of the remaining ammonia. The remaining vapor is first diverted to a vacuum pump and further diverted to a conventional air scrubber or directly to the atmosphere. Here the $CO_2$ is also emitted to the atmosphere. This is important because the final N-fertilizer is free of bicarbonate and thus a stable product in the form of ammonia and/or ammonium sulphate.
11. The cooling tower, which operates by evaporating aqueous liquid to the atmosphere thus providing the cooling effect. Not shown in the figures.
12. P1. P2. P3. P4. The capsule vacuum blowers produce the vacuum.
13. Pipe flange.
14. Pipe flange.
15. Pipe flange.
16. Pipe flange.
17. Pipe flange.
18. Blind flange.
19. Blind flange.
20. Main pipe connection between the evaporator E and the shunt S.
21. Manifold between the evaporator E and the shunt S.
22. Manifold between the evaporator E and the shunt S.
23. Manifold between the evaporator E and the shunt S.
24. Pipe inlet between the biogas reactor R and the shunt S.
25. Pipe connection between the first condensing device K1 and the further condensing device K2.
26. Pipe connection between pump 8 and cooling tower (for cooling of H2 and H4).
27. Pipe connection between H2 and H4.
28. Pipe connection between E and pump 6.
29. Pipe connection between E, pump 6 and H6, H3.
30. Pipe connection between E and H6, H3.
31. Pipe connection between K2 and pump 7.
32. Pipe connection from S to bioreactor R.
33. Pipe connection between S and H2.
34. Pipe connection between H3 and K3.
35. Pipe connection between H3 and H4.
36. Pipe connection from H4 to an ammonia storage tank via a phase separator B2. The second condensed aqueous liquid medium comprising ammonia and vapor not condensed by the second condensing device from K4 are separated in a phase separator B2, where the aqueous liquid medium comprising ammonia is diverted to a storage tank and the vapor not condensed by the second condensing device to an air scrubber or directly to the atmosphere.
37. Pipe connection between pump 7 and K3.
38. Pipe connection between H6 and external supply of waste heat (warm aqueous liquid at 70-90° C.).
39. Pipe connection for return of cooled aqueous liquid between H6 and external heat source.

40. Vacuum manifold to pressurize K2.

41. Aqueous liquid supply to the shunt S (for cleaning in place of S filter elements) and condensing device K2.

42. Exhaust vapor from vacuum blowers to air scrubber.

Figure 3:
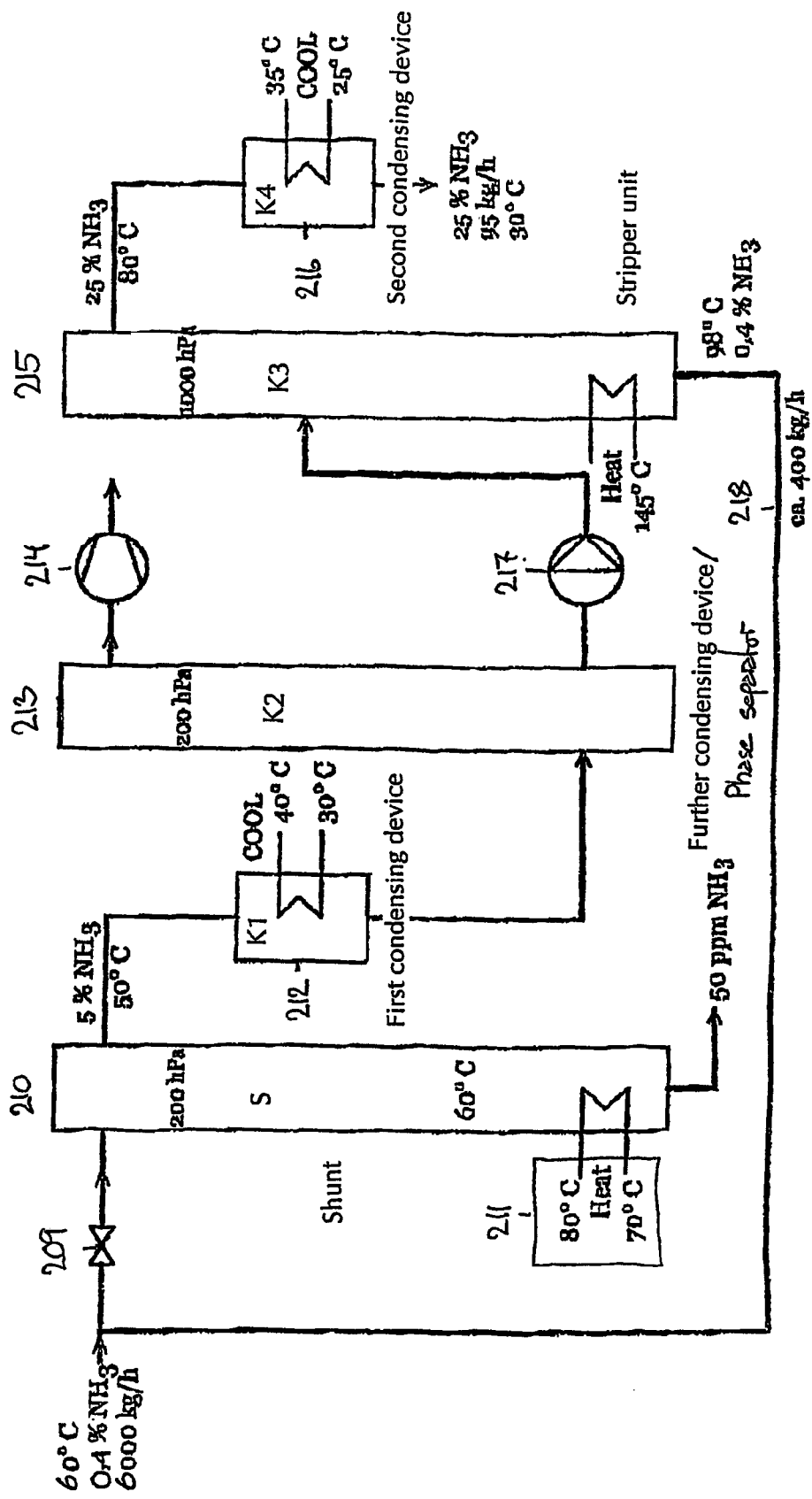
FIG. 3 illustrates one preferred embodiment of the shunt, the stripper unit and associated condensing device(s) of the present invention.

FIG. 3 illustrates yet another embodiment of the stripper device of the invention. The device comprises a first stripping unit 210 and a second stripping unit 215, said units being connected by conduits so that vapor, here about 5% by weight of $NH_3$ at about 50° C., from the first stripping column 210 is condensed by a first condenser 212. Subsequently the condensate and vapor is separated into a condensed phase and a vapor phase at said reduced pressure in a phase separator 213. The condensed phase, here about 5% by weight of $NH_3$ at about 30-40° C., is pumped to said second stripping unit 215 at a reference atmospheric pressure, here atmospheric pressure (1000 kPa), by means of pump 217. In the second stripping unit, the condensed phase is further stripped to produce a vapor of about 25% by weight of $NH_3$ at a temperature of about 80° C. in the top of the second stripping column. Subsequently this vapor phase is condensed in a second condenser 216 to a temperature at about 30° C.

The liquid to be treated, here liquid of manure from an organic waste water treatment plant producing bio gases and treating liquids of manure, is let into said first stripping column 210 through a reduction valve 209 at a temperature of about 60° C.

Said first stripping unit 210 comprises a stripping container 211 for producing a vapor of volatile components from the liquid at a reduced pressure, here e.g. 200 to 800 hPa below a predetermined reference pressure, here preferably atmospheric pressure. Heat is supplied by a heating means; here a heat exchanger placed at the bottom end of the stripping column 210, which heat exchanger here uses cooling water from the biogas production section of organic waste water treatment plant.

Typically said stripping container is a stripping column the characteristics of which has been design according to methods known in the art, including but not limited to designs based on the commercial software design package Hyses™. Typically, it is preferred to use stripping columns having 8-12 theoretical plates. A practical construction of such a stripping column, including design of column plates, inter-plate conduits, selection of column package materials, etc., is known to a person skilled in the art. Commercial stripping columns are generally available from chemical engineering suppliers.

Selecting a proper balance between the energy sources available at the plant site, e.g. either a source of low valued energy such as cooling water or a high valued energy such as combustion heat or electricity, and the involved temperatures and pressures in generating the vapor and condensate, a skilled person can provide an optimum design for the apparatus for vapor stripping of volatile components from a liquid, e.g. for generating vapor of said volatile components.

In a preferred embodiment of the apparatus, heat at about 80° C. is supplied to the column at a rate providing a warm vapor of about 5% by weight of $NH_3$ at a temperature of about 50° C. at the outlet of the column and of a pressure of about 200 kPa.

A residue is taken out of the stripping column, here at the bottom thereof.

A first condenser 212, here a plate type condenser especially suited to resist basic conditions of ammonia which is generally available from chemical engineering suppliers, is used for condensing said vapor of volatile components from said stripping container at said reduced pressure.

A phase separator 213 separates said condensed volatile components and said vapor of volatile components from said first condenser 212 into a condensed phase and a vapor phase at said reduced pressure.

At least one vapor evacuation pumps 214, here preferably a displacement pump generally available from chemical engineering suppliers, is used for removing dissolved gasses such as carbon dioxide and nitrogen and producing a reduced pressure below said reference pressure; said vapor evacuation pumps being positioned down stream said first condenser. Vapor gasses are taken out from the vapor phase of the phase separator 213 to final scrubbing before being released to the atmosphere (not shown).

Said a second stripping unit 215 comprises a second stripping container 215 for producing a vapor of volatile components from said condensed phase at said predetermined reference pressure.

The second stripping container preferably consists of a stripping column which preferably is prepared by same and/or similar methods and means to those used for making said first stripping column 210, with the exception that considerations be taken for a preferably smaller size of the second stripping container column, and for the second stripping container being operated at a higher pressure, e.g. typically operated at predetermined reference pressure about atmospheric pressure (1000 hPa) compared to an operational pressure of about 200 hPa for the first stripping container.

Said second stripping unit further comprises a second condenser 216 for condensing said vapor of volatile components at said predetermined reference pressure. This second condenser is preferably prepared by same and/or similar methods and means to those used for said first condenser 212.

A pumps 217, here a centrifuge type pump generally available from chemical engineering suppliers, is used to pump said condensate from said phase separator 213 to said second stripping column 215.

A residue of the second stripping column, here an aqueous solution of about 0.4% by weight of $NH_3$ at about 98° C., is circulated 218 to the inlet of the first stripping column and there admixed to the inlet liquid.

Figure 4:
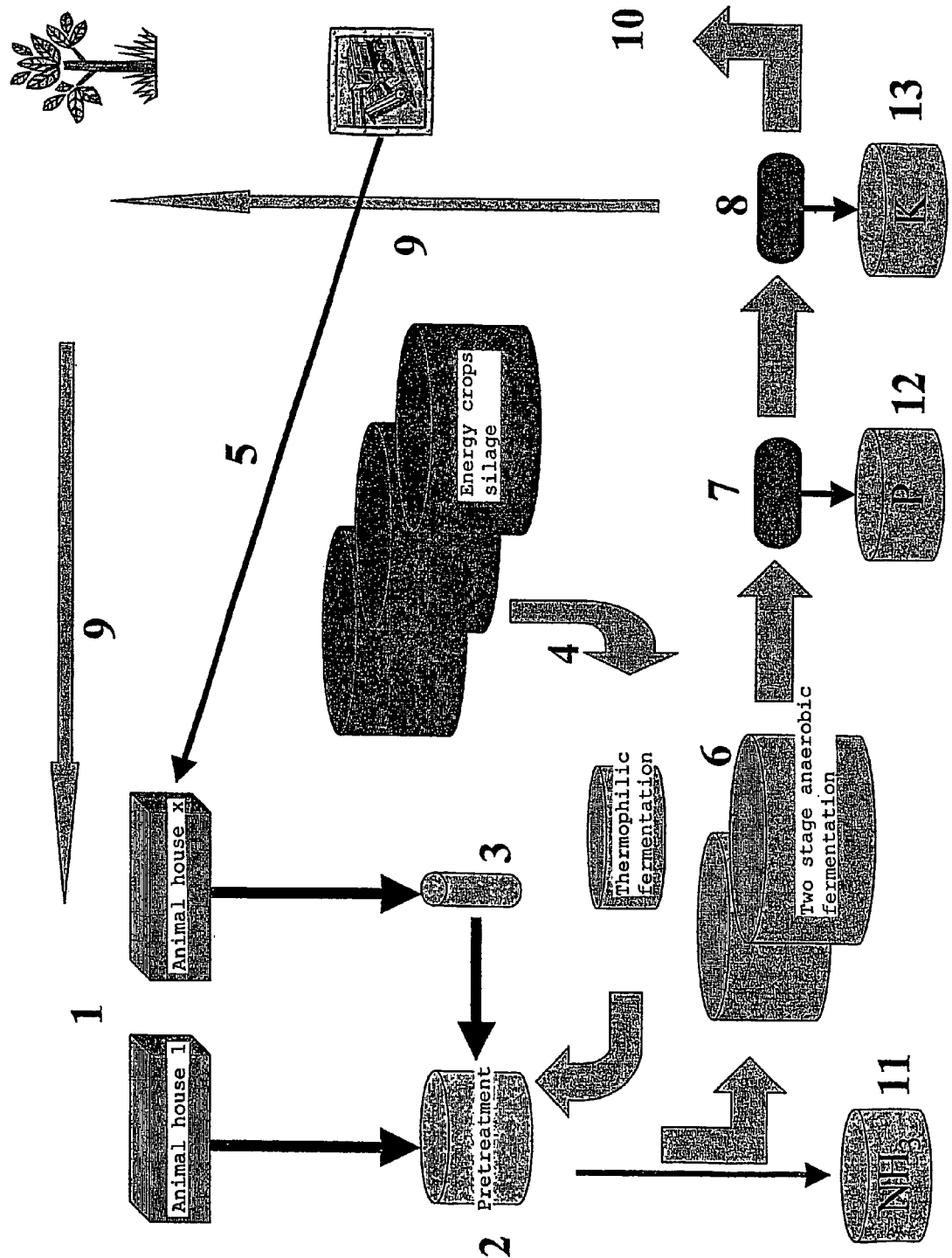
FIG. 4 illustrates possible ways of integrating the shunt, the stripper unit and associated condensing device(s) of the present invention with one or more fermentors or biogas reactor(s) forming part of a plant for processing organic material.

FIG. 4 illustrates the principle of the integration of the shunt/stripper device(s) of the present invention into a plant for processing organic material. The plant is described in more detail herein below. In FIG. 4, manure, preferably in the form of a slurry, generated in a house or stable (1) for the rearing of animals, including domestic animals, such as pigs, cattle, horses, goats, sheep; and/or poultry, including chickens, turkeys, ducks, geese, and the like, is transferred to either one or both of a first pretreatment tank (2) and/or a second pretreatment tank (3). Additional organic material not originating from an animal house on a farm can also be processed and/or subjected to pretreatment. Examples include animal and poultry carcasses, meat and bone meal, and similarly processed products.

The working principles are that the manure, preferably in the form of a slurry including, in one embodiment, water such as reject water used for cleaning the animal house or stable, is diverted to the first pretreatment tank comprising a stripper tank, where ammonia is stripped by means of addition to the stripper tank of e.g. CaO and/or $Ca(OH)_2$. However, addition of CaO and/or $Ca(OH)_2$ to the slurry may also take place prior to the entry of the slurry into the first treatment tank or stripper tank.

At the same time as the addition of CaO and/or $Ca(OH)_2$, or at a later stage, the pretreatment tank comprising the stripper tank is subjected to stripping and/or heating, and the stripped N or ammonia is preferably absorbed prior to being stored in a separate tank (11). The stripped N including ammonia is preferably absorbed to a column in the stripper tank comprised in the first treatment tank before being directed to the separate tank for storage. As ammonia can also be generated during a subsequent fermentation process, the initial stripping process described herein above can be combined with the shunt/stripper devices disclosed in the present invention in order to remove ammonia which is not generated until fermentation of the optionally pre-treated organic material takes place.

Organic materials difficult to digest by microbial organisms during anaerobic fermentation are preferably pretreated in a second pretreatment tank (3) prior to being directed to the first pretreatment tank (2) comprising the stripper tank as described herein above. Such organic materials typically comprise significant amounts of e.g. cellulose and/or hemicellulose and/or lignin, e.g. preferably more than 50% (w/w) cellulose and/or hemicellulose and/or lignin per dry weight organic material, such as straws, crops, including corn, crop wastes, and other solid, organic materials. N including ammonia is subsequently stripped from the pretreated organic material.

In both the first and the second pretreatment tank, the slurry is subjected to a thermal and alkali hydrolysis. However, the temperature and/or the pressure is significantly higher in the second pretreatment tank, which is therefore preferably designed as a closed system capable of sustaining high pressures.

The slurry having optionally been subjected to a pre-treatment as described herein above is preferably diverted to at least one thermophile reactor (6) and/or at least one mesophile biogas reactor (6). The slurry is subsequently digested anaerobically in the reactors concomitantly with the production of biogas, i.e. gas consisting of mainly methane optionally comprising a smaller fraction of carbon dioxide. The biogas reactor(s) preferably forms part of an energy plant for improved production of energy from the organic material substrate.

The shunt/stripper devices disclosed herein can be operationally coupled to any of the above at least one thermophile reactor (6) and/or at least one mesophile biogas reactor (6). The shunt can further be connected to a pre-shunt degassing unit as disclosed herein. The coupling of the shunt/stripper device(s) to the fermentor(s) can be a permanent coupling, i.e. a fixed system, or it can be a transient coupling involving a mobile unit comprising the shunt/stripper device(s).

The biogas can be diverted to a gas engine, and the energy generated from this engine can be used to heat the stripper tank or used to heat a heating source which can be diverted to the evaporator as disclosed herein, where the heating source is subjected to a reduced pressure, said lowering of the pressure generating cold steam. However, the biogas can also be diverted into a commercial biogas pipeline system supplying household and industrial customers.

The remains from the anaerobic fermentation, still in the form of a slurry comprising solids and liquids, is in a preferred embodiment diverted to at least decanter centrifuge (7) for separating solids and fluids. One result of this separation is an at least semi-solid fraction comprising almost exclusively P (phosphor), such as an at least semi-solid fraction preferably comprising more than 50% (w/w) P (12). In the same step (7), or in another decanter centrifuge separation step (8), a liquid fraction preferably comprising almost exclusively K (potassium), such as at least 50% (w/w) K (13) is preferably also obtained. These fractions, preferably in the form of granulates obtained after a drying step, including a spray drying step or a slurry drying step, preferably comprise P and/or K in commercially acceptable purities readily usable for commercial fertilisers (10). Such fertilisers may be spread onto crops or agricultural fields. The liquids (9) also resulting from the decanter centrifuge separation step, such as reject water, can also be diverted to agricultural fields, they can be diverted back to the stable or animal house, or into a sewage treatment system.

In another embodiment, only phosphor (P) is collected following decanter centrifuge separation, and water in the form of reject water is collected in a separate tank for further purification, including further removal of N, removal of odours, and the majority of the remaining solids. This may be done e.g. by aerobic fermentation. Potassium (K) can also be separated from the liquids at this stage.

In a further preferred embodiment, the first pretreatment tank can optionally be supplied with organic material originating from silage stores (4) comprising fermentable organic materials. The divertion of such organic materials to the first pretreatment tank may comprise a step involving an anerobic fermentation such as e.g. thermophilic fermentation tank capable of removing gasses from the silage. Additionally, straws and e.g. crop wastes originating from agricultural fields (5) may also be diverted to stables or animal houses and later to the first and/or second pretreatment tank.

FIGS. 5 & 6 disclose in combination another example of a plant for processing organic material with which the shunt/stripper device(s) of the present invention can be integrated. The different parts of the plant is disclosed herein below in more detail.

Animal Houses

The animal houses (Component number 1) serves to provide an optimal food safety and food quality, an optimal animal welfare and working conditions for the labour personal in the housings, an optimal slurry management, suitable for processing as disclosed herein, and a reduction of emissions to the external environment to a minimum (ammonia, dust, odour, methane, dinitrogen oxide and other gasses).

The housing system can consist of one or more early weaning houses with a total of e.g. 10 sections designed to produce about 250 livestock units annually. Each section houses e.g. 640 piglets (7-30 kg) or 320 slaughter pigs (30-98 kg).

An amount of about 10.000 m3 slurry can be expected to be produced annually from such animal houses. In addition to this volume an amount of 5-10.000 m3 process water shall be recycled through the houses.

Slurry Collection Tank

The function of a slurry collection tank (Component number 2) is to collect slurry form the daily flushings of the animal houses and to work as a buffer before pumping to the main reception tank. The slurry is diverted to the collection tank by means of gravitation. The volume of the tank can be anything appropriate, such as e.g. about 50 $m^3$. The tank can be made of concrete and it can be placed below the floor in the animal houses so that the slurry form the houses can be diverted to the collection tank be means of gravitation.

Main Reception Tank

Slurry from the collection tank is preferably pumped to the main reception tank (Component number 3). Other types of liquid manure/waste, such as e.g. meat and bone meal, can also be added to the reception tank from other farms/processing plants. Besides meat and bone meal, mink slurry, cattle slurry, molasses, vinasses, silage etc. can be added to the main reception tank. The material can transported to the reception tank by lorry and can be loaded directly into the reception tank. The volume/capacity is anything appropriate, such as e.g. about 1.000 m³. The level in the stripper and sanitation tank (12, see below) preferably controls a pump, which pumps slurry from the reception tank to the stripper and sanitation tank. The dose adjustment can be manual or automatic. The maximum capacity can be anything appropriate under the circumstances.

CaO Addition

When slurry is being pumped from the reception tank 3 to the stripper and sanitation tank 12, lime is added to the slurry in order to increase the pH. The lime addition manifold is preferably adjusted to add 30-60 g CaO/kg (dry weight). The lime is preferably supplied as a powder which can be blown into the silo from the lorry. The volume/capacity of the silo can be e.g. about 50-75 m³. The dose of 30-60 g/kg (dry weight) corresponds to app. 6-12 kg CaO per hour with a slurry capacity of 3.5 m³/h with 6% (dry weight).

When added directly to the slurry (6% dry weight), the lime dose is about 60 g/kg (dry weight) yield (about 8.8 kg CaO per hour). It is however preferred to add the lime directly to the alkali pressure sterilazation and hydrolysis unit. When lime is added directly to the pressure unit (the E-media hold 20-70% (dry weight)), the lime dose is about 30-60 g/kg (dry weight). 60 g/kg (dry weight) equals about 342 kg CaO per batch, while 30 g/kg d.m. equals about 171 kg CaO per batch.

Balance Installation

An optional balance (Component number 5) can weigh the incoming E-media (energy containing organic material). The suppliers will preferably specify the type of media which is supplied to the plant, i.e. deep litter, energy crops etc. of various sorts.

The specification shall be made by selecting the relevant E-media on a control panel. According to the suppliers panel registration, the weight of received E-media incl. specification of media can be recorded.

Reception Station for Deep Litter and Energy Crops

An optional reception station (Component number 6) shall receive deep litter from e.g. poultry or other animals as well as energy crops. The station is preferably a large silo equipped with several screw conveyors in the floor. The lorries will empty their load of E-media directly into the silo. The volume/capacity can be anything appropriate under the circumstances, such as e.g. a yearly capacity of E-media (about 51.5% (dry weight)) of about 9.800 tonnes. The volume of the silo can be from several cubic meters to about 100 m³, corresponding to three days capacity (65 hrs). The materials are preferably concrete/steel.

The reception station is connected to the lime pressure cooker via a transport and homogenization system.

Silo for Energy Crops

An optional silo for energy crops (Component number 7) serves to provide storage means for energy crops. The crops are preferably conserved as silage. The volume/capacity can be e.g. from about 5.000-10.000 m³. The silo can be a closed compartment from which silage juice is collected and pumped to the reception tank. The silage can be degassed and/or fermented before being diverted to the reception station.

Transport- and Homogenisation System for Deep Litter and Energy Crops

A transport- and homogenisation system (Component number 8) for deep litter and energy crops preferably receives E-media from the screw conveyors in the floor of the reception station. The E-media can be transported by additional screw conveyors to the cooking units and at the same time preferably macerated by an integrated macerator. The volume/capacity can be anything required under the circumstances including about 1.5 m3 E-media/hour, or 8.200 tonnes of E-media/year. The capacity of the transport-homogenisation system is preferably not less than about 30 m3/hour. Three fundamental parameters shall control the addition of E-media, i.e. volume, weight per volume, and time. From these parameters volume per unit time, time and thus total volume and weight shall be established.

Alkali Pressure Sterilization and Hydrolysis Unit

An alkali pressure sterilization and hydrolysis unit, such as a lime pressure cooker, (Component number 9) shall serve two main purposes, i.e. firstly elimination of microbial pathogens in the E-media in particular in deep litter from various poultry or other animal productions and secondly, at the same time hydrolyse structural components of the litter in order to render them available for microbial degradation in the fermentors.

The unit shall also preferably eliminate or at least substantially reduce any vira and/or BSE-prions if present in waste introduced into the plant. Such waste include meat- and bone meal, animal fats or similar produce from the processing of animals not used for consumption. In this way it is envisaged that e.g. meat and bone meal originating from cattle potentially infected with BSE can be used in accordance with the present invention. Similarly, poultry having contracted diseases sudh as e.g. Newcastle disease can also be used.

Filling of the pressure sterilizer is provided by the transport- and homogenisation system, which transports E-media into the according to type of E-media as defined on the balance installation.

The alkali pressure sterilization and hydrolysis unit generates a number of different 30 gasses and other undesirable odourants. Examples include:

Carboxylic acids

Alcohols

Phenolics

Aldehydes

Esters

Nitrogen heterocycles

Amines

Sulphides

Thiols (mercaptans)

The above compounds are either acidic, basic or neutral. Accordingly, the absorption column preferably comprises three columns in order to take account of the different chemistries needed in order to neutralize these compounds.

The gas phase generated in the alkali pressure sterilization and hydrolysis unit is initially diverted to an absorber complex comprising i) base-absorber capable of removing acidic components, then the gas phase is diverted to ii) an acid absorber capable of removing basic components such as e.g. ammonia and amines, and finally the gas phase is diverted to iii) a hypochlorite absorber capable of oxidizing the neutral compounds.

The alkali pressure sterilization and hydrolysis unit preferably comprises an elongated chamber with inlet(s) and outlet(s) port(s) for the organic material. A stirrer is located in the center of the elongated chamber. Hot vapor/steam is used for heating the organic material. The steam can be entered directly into the chamber.

Solid organic material can be diverted to the alkali pressure sterilization and hydrolysis unit via a valve. Liquid organic material can be diverted to the alkali pressure sterilization and hydrolysis unit via a nozzle or a connecting piece. The alkali pressure sterilization and hydrolysis unit also comprises an outlet for diversion of gasseous substances to the absorber complex described herein elsewhere.

The operating parameters are as follows:

| | |
|---|---|
| Pressure: | 2-10 bar |
| Temperature: | 100-220° C. |
| Processing time: | Preferably less than 2 timer (about 40 min. at 160° C.) |

After processing in the alkali pressure sterilization and hydrolysis unit, the pressure can be lowered by diversion of cold biomass or organic material to the alkali pressure sterilization and hydrolysis unit. The processed organic material is preferably removed from the alkali pressure sterilization and hydrolysis unit while still under some pressure.

Mixing Tank for Pressure-sterilized E-media and Raw Slurry

Following sterilization and hydrolysis in the pressure unit, the treated biomass is allowed to expand into a mixing tank (Component number 10) preferably located below the pressure unit. Excess pressure (steam) is released into the stripper and sanitation tank in order to collect ammonia and transfer heat to the stripper tank biomass before expansion into the mixer tank.

The purpose of the mixer tank is to mix cold raw slurry from the reception tank with hot sterilized E-media in order to obtain heat transfer (re-use of heat) and mixing of the two media.

The volume/capacity is e.g. about 25 m$^3$. Any suitable material can be used, including insulated glasfibre. The working temperature is typically about 70-95° C.

Tank for Liquid Biomass

The liquid biomass contained in the tank for liquid biomass (Component number 11) can be used to ensure sufficient biogasproduction during the start up phase of the whole plant. However, it can also be used occasionally, when such liquid biomass is available. Liquid biomass include e.g. fish oil, and animal or vegetable fats. Vinasses and molasses can also be used, but this is not preferred because of the relatively high water content and thus low potential energy content per kg product.

The volume/capacity is typically about 50 m$^3$, and a suitable material for the tank is stainless steel. The contents of the tank is preferably liquids and solids having a particle size of max. 5 mm. Stirring as well as a heating system for temperature control is preferably provided, as are feeding pump(s) to the fermentor(s). The temperature shall preferably be min. 75° C. so that oily or fatty biomass can be pumped into the fermentor(s).

Stripper and Sanitation Tank

The stripper and sanitation tank (Component number 12) preferably receives the following media:

Slurry from reception tank (3) and/or

E-media from the pressure cooker (9), and/or

Possibly liquid biomass from biomass liquid tank (11), and/or

Reject water from decanter (18) or possibly after K-separation (25).

The purpose of the tank is to regenerate heat used in the pressure cooker by heating the slurry from the reception tank, to mix the E-media with slurry and hence to produce a homogeneous feed to the fermentors, to control pH before feeding to fermentors, and to sanitise the slurry.

The stripper and sanitation tank strips ammonia, and ammonia fluid is diverted to an absorption column. Microbial pathogens are eliminated and the media/slurry is prepared for anaerobic digestion.

The stripper and sanitation tank supplies the fermentor(s) with pre-treated material for fermentation. In a timed process the material will be transported to the fermentors. The demand of material depends on the digestion process in the fermentors. One, two, three or more fermentors can be employed.

The stripper and sanitation tank is regularly filled with slurry and E-media from the alkali pressure process. Finally, to obtain a dry matter of about 15% (dry weight) one or more level switches regulate the content in the tank. A (dry weight)-mesuring unit regulates the content of (dry weight). Every e.g. 1 hour after filling of slurry and E-media it is possible to pump E-media to the fermentor(s).

The top of the stripper and sanitation tank is preferably ventilated through an ammonia-absorbing unit, and a pH-measuring unit regulates the need for CaO. A timed process can optionally pump water/slurry into the drizzle system to prevent production of foam.

Fermentors for Biogas Production

Digestion of the biomass is provided by a multi-step fermentor system preferably comprising three fermentors (Components 13, 14 and 15). Systems with fewer as well as more fermentors can also be applied.

The fermentors are preferably connected to achieve maximum flexibility and optimum biogas production. The fermentors shall be planned for routinely running at termofile (45-65° C.) as well as mesofile (25-45° C.) temperatures, respectively. Regulation of pH is possible through addition of an organic acid (liquid) in necessary quantities.

The fermentors preferably receives the following media:

E-media from the stripper and sanitation tank (12)

Liquid biomass from the liquid biomass tank (11)

Acids from the acid tank (16)

The running conditions can be any conditions suitable, including

| | |
|---|---|
| Media: | All sorts off animal manure, primarily pigs slurry. Macerated energy crops. Some sorts of organic waste, CaO, organic Acids |
| Running temperature: | 35-65° C. |
| Running gas combination: | 65% $CH_4$, 33% $CO_2$, 2% other gases |
| Insulation k-value: | 0.25 W/m$^2$K heatloss is estimated to 10 kW |
| Running Max. Pressure: | +20 mbar abs. (No vacuum) |
| Max. viscosity in media: | 12% (dry weight) |
| Base/Acid-range: | 5-10 pH |
| Abrasive rudiments in media (Ex. Sand): | 1-2% |
| Max. temperature in heating elements: | 80 degrees celcius |
| Max. effects in heating elements: | 600 kW |
| Transmission effect: | 7.5 kW/20-25 rpm |

The digestion shall preferably be run at from about 55° C. to about 65° C., such as at about 60° C. as disclosed herein in more detail elsewhere. Heat loss is estimated to about 10 kW. The biomass in the tank is can be heated from 5° C. to 55° C. during 14 days, with the possibility of addition of acid for adjustment of pH.

The shunt/stripper device(s) as disclosed in detail herein elsewhere is preferably operationally linked to the above fermentor(s) in order to remove ammonia and thereby preventing any undesirable excess of ammonia in the fermentors. A "pre-shunt" degasser can optionally be included as described herein elsewhere.

The generated biogas can e.g. be diverted to a gas engine/motor capable of heating a heating source which can subsequently be diverted to the evaporator. Following a lowering of the pressure cold steam is generated. The cold steam is diverted to the shunt for stripping off ammonia and optionally also other volatile compounds.

Tank for Organic Acids for pH Adjustments in Fermentors

A tank for organic acids (Component number 16) for pH adjustments in the fermentor(s) is preferably also provided.

Buffer Tank for Degassed Slurry before Decanter

Following digestion of the biomass in the fermentors the degassed biomass is optionally pumped to a buffer tank (Component number 17) before being subjected to separation in the decanter. The biomass can also be diverted directly to a decanter installation as described below.

Decanter Installation

The function of the decanter installation (Component number 18) is to extract suspended solids (ss) and P from the biomass.

The decanter separates the digested biomasse into the two fractions i) solids, including P, and ii) reject water.

The solids fraction contains 25-35% d.m. App. 90% of the ss. and 65-80% of the P-content of the digested biomass is extracted. In case of addition of PAX (Kemira Danmark) to the buffer tank before separation in the decanter, app. 95-99% of the P can be extracted. The solids fraction is transported to containers by means of a shaft less screw conveyor.

The rejectwater contains 0-1% ss and dissolved K. The ss depends on the addition of PAX. The principal component of the reject waters is dissolved K which amounts to app. 90% of the original K-content in the biomass. The reject water is pumped to the reject water tank.

P-fraction Transport System and Treatment

From the decanter installation the solid matter fraction (routinely called the P-fraction) can be transported to a series of containers by means of conveyor screws and belts forming a P-fraction transport system (Component number 19).

A common conveyor band transports P-fraction to a storage where it is stacked into miles, covered with a compost sheet and allowed to compost. The composting process further dries the P-fraction and the d.m.-content thus increases to 50-60%.

Second N-stripping Step

Efficient stripping of ammonia from the reject water is preferred, and a residual level of about 10 mg $NH_4$—N/ltr or less is preferred.

The second stripping step can be carried out be using a steam stripper operated at ambient pressure. Examples of preferred steam strippers are disclosed herein elsewhere.

The stripper principle benefits form the different boiling temperatures of ammonia and water. At temperatures close to 100° C. extraction of ammonia is most efficient.

The use of energy in order to heat the feed is an essential running parameter. The stripper unit shall therefore preheat the feed before entering the stripper column to close to 100° C. This can be provided by using steam (or possibly warm water and steam) from a motor generator unit in a steam-water heat exchanger.

When heated the feed enters the stripper column and percolates over the column while at the same time being heated to the running temperature by a counter current of free steam. The steam/ammonia gas is subsequently condensed in a one or two step condensator. From the floor of the column the water now essentially free of ammonia is pumped to a level controlled exit pump.

The stripped ammonia can be diverted to the bottom of a two-step scrubber condensator where the ammonia gas is condensed primarily in a counter current of cooled ammonia condensate. The ammonia gas not condensed can optionally be condensed in a counter current of pure water (possibly permeate from the final reverse osmosis step). If the use of acid is desirable or necessary it is appropriate to use sulphuric acid at this stage. It is thus possible to achieve a higher final concentration of ammonia. The scrubber condensator is preferably constructed from a polymer in order to allow the use of acids.

The second end-stripping strip is preferably carried out by using the stripper device described herein above (i.e. without the device being connected to the shunt, but instead).

Ammonia Absorption Column (for use with First and/or Second N-stripping)

In one embodiment, a condensate scrubber can be used in order to gain flexibility concerning addition of acid. The column (Component number 21) is preferably constructed in two sections so that the fraction of ammonia not condensed in the first section is subsequently condensed in the second section. This takes place in a full counter current so that addition of water is limited as much as possible. Thereby a maximum ammonia concentration in the final condensate is reached (about or more than 25%). The ammonia product can be pumped out with a separate pump or be taken out from a valve on the circulation pump. The absorption may be assisted by addition of sulfuric acid into the water counter current.

The ammonia absorption column is preferably an acid absorber, and the column forms part of an absorber complex comprising i) base-absorber capable of removing acidic components, ii) an acid absorber capable of removing basic components such as e.g. ammonia and amines, and iii) a hypochlorite absorber capable of oxidizing the neutral compounds.

Sulphuric Acid Tank

The sulphuric acid tank is used for storing the sulfuric acid used in the N-stripping process. (Component number 22).

NS Tank

The NS tank (Component number 23) is used for storing the stripped N.

Gas Store

It is preferred to establish a gas store (Component number 24) as a bufferstore for the feeding of e.g. a motorgenerator engine.

Rejectwater Tank

From the decanter installation the rejectwater is preferably pumped to the rejectwater tank (Component number 25).

The rejectwater tank is equipped with a submerged microfilter with static operation. The micro-filter shall remove particles larger than 0.01-0,1 µm. A negative pressure of 0.2-0.6 bar can be built up at the membrane. Hence the permeate is sucked through the membrane retaining the particles on the membrane surface. In order to prevent membrane fouling and scaling the coating of the membrane surfaces has to be removed by a periodic backwash procedure.

A micro-processor control device shall automatically control the extraction of permeate and the backwash procedure.

The extraction shall be interrupted by periodic backwash e.g. for 35 seconds for every 300 seconds running time. The total flow shall be 2-6 m3 per hr.

Aeration may be applied to assist the micro-filtration. Aeration impose shear stress on the membrane surface reducing scaling and fouling. It further aerates the reject-water and stimulates aerobic decomposition of residual organic matter, nitrification and denitrification. Possible remaining odour, nitrate etc. is thus removed during the process of micro-filtration.

From this tank the permeate shall be used for:

Rinsing of the animal houses, canals, slats etc.

Further separation. Dissolved K shall be concentrated by means of reverse osmosis, the K-fraction being stored in a separate storage tank. Water for rinsing animals houses may also be taken form this permeate flow.

The K may also be concentrated through other means such as mechanical or steam compression. This depends on the specific choice for each specific plant and amount of excess heat available for steam compression.

The reject water tank containing the concentrate from the micro-filtration shall be emptied at regular intervals to remove the particle concentrate. This shall be added to either the K-fraction or the P-fraction from the decanter.

K tank

The K tank (component number 26) serves the purpose of storing the potassium (K) concentrate.

Gas Cleaning

The biogas produced in the fermentors may contain trace amounts of hydrogen sulfide ($H_2S$) which are necessary to remove (Component number 27) before burning the biogas in a combined heat and power plant.

The gas shall be cleaned by employing the ability of certain aerobic bacteria to oxidise $H_2S$ into sulfate. The genus shall primarily be the genus Thiobacillus which is known form several terrestrial and marine environments. Other genus may also be used such as Thimicrospira and Sulfolobus.

A tank made of glass fiber packed with plastic tubes with a large surface area shall be rinsed with reject water to maintain the packing material moist. The biogas is diverted through the packed column and an air stream (of atmospheric air) is added to the biogas stream. The atmospheric air is added to provide an oxygen concentration of 0.2% in the gas stream, i.e. sufficient to oxidize the $H_2S$ and therefore not to produce an explosive mixture of biogas and oxygen. A ring side blower is used.

Combined Heat and Power plant (CHP)

The main component in the CHP (Component number 28) can be e.g. a gas fired engine connected to a generator for production of electric power. The main priority for the CHP is to produce as much electric power as possible relatively to heat. The engine is preferably cooled by a water circuit (90° C.) and the generated heat is preferably used in the plant process and/or to the heating of e.g. the animal houses.

The exhaust gas is used in a recuperator for steam production. The steam is used as heating source in the plant process, i.e. in the pressure sterilization unit and in the n-stripper. Depending on the amount of steam it may also be used for concentrating the K in the rejectwater (seam evaporation).

The generated heating source is also capable of being diverted to the evaporator operationally linked to the shunt. A lowering of the pressure in the evaporator results in the generation of cold steam which can be diverted to the fermentation liquid contained in the shunt. Volatile compounds such as e.g. ammonia can be stripped at least partly from the fermentation liquid in this way as described herein elsewhere, and the at least partly stripped fermentation liquid in the shunt can be returned to the fermentor.

Between the steam and heat circuit, there will be installed a heat exchanger, so it is possible to transfer heat from the steam system to the heat system. In addition to the above mentioned genset there will be installed a steam boiler. This boiler will be used for heat production to start the process, and in addition be used as a backup for the genset. If there is produced more steam than needed in the plant process, the rest production can be flashed of in a cooler.

To start the plant process (heating of fermentor tanks) etc., heat is provided by e.g. an oil fired boiler. As soon as gas production is achieved the oil burner will be switched to a gas burner. As soon as gas production is large enough to start the engine, the engine will take over the heat production.

Potassium Separation

At least two alternatives for separating potassium from the rejectwater are possible (Component number 29). At relatively high levels of biogas production the motor-generator engine produces excess heat (steam at 160° C.) which can be used to concentrate the K. The distillate free of nutrients may be used for field irrigation or recycled through the whole plant.

At relatively low rates of biogasproduction a micro-filter can be used to filter particles larger than 0.001 μm, such as larger than 0.01 μm, for example larger than 0.1 μm from the reject water rendering the permeate suitable for treatment in a standard reverse osmosis filter. The K shall preferably be concentrated to a 5-15% (v/v) solution, optionally a 10-20% (v/v) solution.

The invention claimed is:

1. A system comprising a stripper device for stripping volatile compounds from a liquid medium, said stripper device comprising:
   a) a shunt to which aqueous liquid medium comprising volatile compounds can be diverted in the form of a side stream to at least one fermentor and/or at least one biogas reactor,
   b) means for diverting aqueous liquid medium comprising volatile compounds to the shunt from said at least one fermentor and/or at least one biogas reactor,
   c) an evaporator device comprising a sample of aqueous liquid to which heat obtained from an external heat source can be added, wherein a reduction of the pressure in said evaporator to a first pressure below a predetermined reference pressure generates cold steam,
   d) means for directing the cold steam generated by the evaporator of c) through said aqueous liquid medium comprising volatile compounds in the shunt of the stripper device at said pressure below a predetermined reference pressure, thereby stripping off volatile compounds and obtaining a cold, volatile compound-comprising steam,
   e) a first condensing device,
   f) means for diverting said cold volatile compound-comprising steam at said pressure below the predetermined reference pressure to the first condensing device, and condensing in a first condensing step in said first condensing device said cold volatile compound-comprising steam at said pressure below a predetermined reference pressure, thereby obtaining a first condensed aqueous liquid medium comprising said volatile compounds and vapor not condensed by the first condensing device, g) a stripper unit for stripping volatile compounds at said predetermined reference pressure or at a second pressure higher than said predetermined reference pressure,
h) means for diverting said first condensed aqueous liquid medium comprising volatile compounds obtained in f) to the stripper unit, and stripping off at least part of the volatile compounds from said first condensed aqueous liquid medium comprising volatile compounds by injecting hot aqueous steam at said reference pressure or at the higher second pressure, thereby obtaining a hot volatile compound-comprising steam and aqueous liquid stripped off at least part of said volatile compounds,
i) a second condensing device, and
j) means for diverting said hot volatile compound-comprising steam to a second condensing device, and condensing said hot volatile compound-comprising steam, thereby obtaining a condensate comprising volatile compounds.

2. The system according to claim 1, wherein the stripper device further comprises a further condensing device and means for diverting said vapor not condensed by the first condensing device to the further condensing device for removing at least some of the remaining volatile compounds from said vapor not condensed by the first condensing device, said further condensation involving the step of washing the vapor in a counter current of aqueous liquid, thereby obtaining a combined aqueous liquid fraction comprising the first condensed aqueous liquid medium from the first condensing device and volatile compounds condensed in the further condensing device, and optionally vapor not condensed by the further condensing device.

3. The system according to claim 2 further comprising means for diverting said combined aqueous liquid fraction to the stripper unit.

4. The system according to claim 2, wherein the stripping of volatile compounds in the stripper unit results in the formation of a stripped aqueous liquid medium comprising at the most 200 ppm volatile compounds.

5. The system according to claim 4, wherein said second condensing device comprises two heat exchangers for cooling said hot volatile compound-comprising steam in two steps, said cooling generating said condensate comprising volatile compounds in two steps, said second condensing device further generating a heating source, said system further comprising means for directing said heating source to said evaporator for heating aqueous liquid in said evaporator.

6. The system according to claim 1 further comprising means for diverting aqueous liquid medium stripped for essentially all of said volatile compounds from said stripper unit to said shunt.

7. The system according to claim 1 wherein the shunt further comprises a pre-degassing unit for removing at least one undesirable gas affecting ammonia stripping from the organic material before the remaining part of the organic material is contacted by the cold steam generated by the evaporator.

8. The system according to claim 7 wherein each undesirable gas is selected from the group consisting of methane, carbon dioxide and hydrogen disulphide.

9. The system according to claim 1, wherein said reference pressure is 1 bar.

10. The system according to claim 9, wherein the first pressure is from about 0.05 to about 0.4 bar.

11. The system according to claim 9, wherein the second pressure is from about 2 to 3 bar.

12. The system according to claim 9, wherein the first pressure is from about 0.1 to 0.2 bar.

13. The system according to claim 9, said system further comprising at least one air scrubber for cleaning said vapor not condensed by the first condensing device and/or said vapor not condensed by the second condensing device.

14. A mobile unit comprising the system according to claim 1, wherein said mobile unit can be connected to a fixed installation in the form of at least one fermentor and/or at least one biogas reactor.

15. A plant for processing organic material comprising solid and liquid parts, said plant comprising the system according to claim 1, said plant further comprising at least one fermentor and/or at least one biogas reactor, wherein said organic material is fermented at mesophilic and/or thermophilic conditions.

16. The plant according to claim 15, said system further comprising a stripper tank for stripping nitrogenous compounds from the organic material prior to fermentation or biogas production.

17. The plant according to claim 15, said system comprising a pre-treatment tank for hydrolysing organic material prior to an initial stripping of nitrogenous compounds from the organic material and/or prior to fermentation and/or biogas production of the organic material.

18. The plant according to claim 15, said system further comprising a lime pressure cooker for hydrolysing organic material.

19. The plant according to claim 15, said system further comprising at least one silage storage tank for generating ensiled plant material.

20. The plant according to claim 19, said system further comprising a pre-treatment fermenting tank for fermenting silage and/or lime pressure cooked organic material, in which the fermentation conditions are selected from mesophilic fermentation conditions and/or thermophilic fermentation conditions.

21. The processing plant according to claim 15 comprising
i) a lime pressure cooker for hydrolysing the organic material,
ii) a stripper tank for stripping ammonia from said lime pressure cooked organic material, and
wherein said at least one fermentor and/or at least one biogas reactor is for fermenting said lime pressure cooked and ammonia stripped organic material.

22. The plant according to claim 21, said system further comprising a reception station for receiving organic material comprising solid parts and a transport and homogenisation system for homogenizing organic material comprising solid parts and transporting the homogenized organic material comprising solid parts to the lime pressure cooker.

23. The plant according to claim 22, wherein the transport and homogenisation system comprises screw conveyors and an integrated macerator.

24. The plant according to claim 22, wherein the reception station is fitted with screw conveyors in the floor of the reception section, and wherein the transport and homogenisation system can receive the organic material comprising solid parts from the screw conveyors located in the floor of the reception station.

25. The plant according to claim 22, wherein the lime pressure cooker is also connected to a reception tank for receiving liquid organic material, wherein liquid organic material can be diverted from said reception tank to said lime pressure cooker.

26. The plant according to claim 21, wherein the lime pressure cooker comprises a single chamber and a stirrer, an entry port for entering organic material to be lime pressure cooked, and an outlet for diverting the lime pressure cooked organic material to a mixing tank or to said at least one fermentor and/or at least one biogas reactor connected to said system.

27. The plant according to claim 26, wherein a container for lime addition is connected to the lime pressure cooker, and wherein the mixing tank connected to the lime pressure cooker is also connected to a reception tank for receiving organic slurries, wherein the mixing tank is used for mixing lime pressure cooked organic material with organic slurries diverted to the mixing tank from a reception tank.

28. The plant according to claim 27, wherein the container for lime addition comprises a by-pass for adding lime directly into the mixing tank.

29. The plant according to claim 27, wherein the mixing tank is connected to the stripper tank so that the mixture of the lime pressure cooked organic material and the organic slurries from the reception tank can be pumped into the stripper tank.

30. The plant according to claim 29, wherein the stripper tank is further connected to the reception tank in order to receive organic slurries from the reception tank and also connected to the lime pressure cooker in order to receive lime pressure cooked organic material from the lime pressure cooker.

31. The plant according to claim 26, wherein the mixing tank and the stripper tank are connected by a macerator for macerating lime pressure cooked organic material and organic slurries to be diverted from the mixing tank to the stripper tank.

32. The plant according to claim 26, wherein the stripper tank is connected to an absorption system comprising a base absorber for absorbing acidic compounds, an acid absorber for adsorbing basic compounds, and a hypochlorite oxidizer for oxidizing neutral compounds.

33. The plant according to claim 32, wherein the acid absorber absorbs ammonia stripped from the stripper tank.

34. The plant according to claim 33, wherein the absorption system is connected to a sulphuric acid tank and to a tank for storing a final ammonia condensate.

35. The plant according to claim 32, wherein the lime pressure cooker is also connected to the absorption system, and wherein any ammonia stripped from the lime pressure cooked organic material is also diverted to the absorption system.

36. The plant according to claim 21, wherein the plant further comprises an animal housing system connected to a collection tank for collection of organic slurries produced by the animals in the animal housing system, wherein the collection tank is connected by a pump to a reception tank for receiving organic slurries so that organic slurries can be pumped from the collection tank to a reception tank.

37. The plant according to claim 36, wherein the collection tank is located below the floor of the animal housing system so that organic slurries can be diverted to the collection tank by means of gravitation.

38. The plant according to claim 21, wherein the system further comprises a pre-treatment fermentation tank for fermenting lime pressure cooked organic material before the lime pressure cooked organic material is subjected to a second ammonia stripping step in the stripper tank for stripping ammonia from said lime pressure cooked and fermented organic material.

39. The plant according to claim 38, wherein the stripper tank and/or the lime pressure cooker is connected to a silage store comprising a fermentable organic material.

40. The plant according to claim 39 further comprising an anerobic pre-treatment fermentation tank capable of removing gasses or odourants from silaged organic material and/or lime pressure cooked organic material, and wherein the silaged organic material and/or the lime pressure cooked organic material can be diverted to the anaerobic fermentation tank before being subsequently diverted to the stripper tank.

41. The plant according to claim 40, wherein the anaerobic pre-treatment fermentation tank is a thermophilic fermentation tank.

42. The plant according to claim 40, wherein the anaerobic pre-treatment fermentation tank is a mesophilic fermentation tank.

43. The plant according to claim 21, wherein the plant further comprises a pre-treatment fermentation tank for fermenting organic material before the organic material is subjected to lime pressure cooking and ammonia stripping.

44. The plant according to claim 21, wherein the stripper tank is connected to at least one fermentor and/or at least one biogas reactor connected to said system.

45. The plant according to claim 44, wherein the at least one biogas producing fermentor is connected to a tank for collection of biogas.

46. The plant according to claim 45, wherein the plant further comprises an outlet for diverting the biogas into a commercial biogas pipeline system.

47. The plant according to claim 44 further comprising a gas cleaning unit for removing hydrogen sulphide and other odourants present in the produced biogas.

48. The plant according to claim 44 further comprising a gas fired engine connected to a generator for production of electric power and heat.

49. The plant according to claim 48, wherein the plant comprises pumps, valves and pipes allowing use of the energy generated by the gas fired engine for heating the stripper tank.

50. The plant according to claim 44 further comprising a liquid biomass tank for diverting liquid biomass to the at least one biogas producing fermentor.

51. The plant according to claim 44 further comprising a decanter centrifuge for separating fermented organic material into a semi-solid fraction comprising 30-40% (w/w) dry matter of which 2 to 10% (w/w) is phosphor, and a liquid fraction comprising reject water, further comprising means for diverting said liquid fraction obtained from said decanter centrifuge to said stripper device.

52. The plant according to claim 51, wherein the pre-filter separates particles larger than 0.1 μm (microns) from the reject water.

53. The plant according to claim 51, wherein the pre-filter separates particles larger than 0.01 μm (microns) from the reject water.

54. The plant according to claim 51, wherein the pre-filter separates particles larger than 0.001 μm (microns) from the reject water.

55. The plant according to claim 51, wherein the permeate is used for flushing manure canals of an animal housing system.

56. The plant according to claim 44, wherein the stripper tank is connected to a biogas producing multi-step fermentor system comprising three fermentors capable of operating at both thermophile conditions and mesophile conditions, wherein each fermentor is connected to said system.

57. The plant according to claim 51 further comprising a reverse osmosis unit for separating potassium from the liquid fraction comprising reject water from which ammonia has been stripped, wherein the reverse osmosis unit comprises a) a pre-filter, and b) a reverse osmosis filter for filtering a permeate resulting from ceramic filtration.

58. The system according to claim 1, further including means for diverting said aqueous liquid medium stripped for at least part of said volatile compounds back to one of the at least one fermentor and/or at least one biogas reactor from which the liquid medium was originally obtained.

59. The system according to claim 1, said system further comprising a phase separator and means for diverting said condensate comprising volatile compounds and vapor not condensed by the second condensing device from said second condensing device to a phase separator for separating said condensate comprising volatile compounds and vapor not condensed by the second condensing device.

60. A method for controlling the fermentation of organic material comprising undesirable volatile compounds, said method comprising the steps of
- a) providing a fermentor comprising a liquid medium comprising organic material and a biomass capable of fermenting said organic material,
- b) diverting said liquid medium to a side stream of the fermentor in the form of a shunt,
- c) contacting said liquid medium in said shunt with cold steam at a first pressure below 1 bar, thereby obtaining a cold steam comprising volatile compounds and liquid medium at least partly stripped for volatile compounds,
- d) condensing said cold steam comprising volatile compounds, thereby obtaining a first condensed liquid medium,
- e) injecting hot steam into said first condensed liquid medium at a second pressure of at least 1 bar,
- f) stripping off at least part of said volatile compounds comprised in said first condensed liquid medium, and obtaining a hot steam of volatile compounds and a condensed liquid medium stripped for essentially all volatile compounds, and
- g) redirecting said liquid medium at least partly stripped for volatile compounds in step c) to said fermentor, and/or returning said condensed liquid medium stripped for essentially all volatile compounds in step f) to said shunt or to said fermentor, wherein said stripping of volatile compounds and said redirection of said at least partly stripped liquid medium controls the fermentation of said organic material.

61. The method of claim 60 wherein said volatile compounds include ammonia and said liquid medium of step a) is reject water.

62. A method for stripping volatile compounds from a liquid medium, said method comprising the steps of
- a) providing an aqueous liquid medium comprising volatile compounds, and
- b) diverting said liquid medium comprising volatile compounds to a shunt operably linked to a heating source and a condensing device,
- c) obtaining cold steam in an evaporator by adding heat to a sample of aqueous liquid and reducing the pressure below a predetermined reference pressure, and
- d) directing said cold steam through said liquid medium comprising volatile compounds in the shunt of the stripper device at said pressure below the predetermined reference pressure, thereby stripping off volatile compounds and obtaining a cold volatile compound-comprising steam, and
- e) diverting said cold volatile compound-comprising steam at said pressure below the predetermined reference pressure to a first condensing device, and
- f) condensing in a first condensing step said cold volatile compound-comprising steam at said pressure below the predetermined reference pressure, thereby obtaining a first condensed aqueous liquid medium comprising volatile compounds, and
- g) diverting said first condensed aqueous liquid medium comprising volatile compound to a stripper unit, and
- h) stripping off the volatile compound from said first condensed aqueous liquid medium comprising volatile compound by heating said first condensed aqueous liquid in said stripper unit at a higher second pressure, and obtaining a liquid with a reduced concentration of volatile compounds.

63. The method according to claim 62, where said predetermined reference pressure is 1 bar.

64. The method of claim 62, wherein the system according to claim 1 is used for operating the method.

65. The method of claim 62, wherein in step f) is further obtained a vapor not condensed by the first condensing device, and said vapor not condensed by the first condensing device is diverted to a further condensing device at said pressure below a predetermined reference pressure, removing part of the remaining volatile compounds from said vapor not condensed by the first condensing device by washing in a counter current of aqueous liquid, obtaining a aqueous liquid fraction comprising volatile compounds and vapor not condensed by the further condensing device.

66. The method of claim 65, wherein in step g) said aqueous liquid fraction comprising volatile compounds is further diverted to said stripper unit, and wherein in step h) volatile compounds are stripped from said first condensed aqueous liquid medium comprising volatile compounds and said aqueous liquid fraction comprising volatile compounds by heating at said second pressure, thereby obtaining a hot volatile compounds-comprising steam and aqueous liquid stripped off at least part of said volatile compounds.

67. The method of claim 66, wherein said hot volatile compound-comprising steam is diverted to a second condensing device, condensing said hot volatile compound-comprising steam at or above said reference pressure, thereby obtaining a second condensed aqueous liquid medium comprising volatile compounds and vapor not condensed by the second condensing device.

68. The method of claim 62, wherein the aqueous liquid medium stripped for at least part of said volatile compounds is returned to the fermentor or biogas reactor from which the liquid medium was originally obtained.

69. The method of claim 68, wherein the aqueous liquid medium returned to the fermentor or biogas reactor is stripped for at least 20% of its content of volatile compounds.

70. The method of claim 62, wherein said predetermined reference pressure is 1 bar.

71. The method of claim 70, wherein the first pressure is from about 0.1 to 0.42 bar.

72. The method of claim 70, wherein the second pressure is from about 1 to 4 bar.

73. The method of claim 62, wherein said volatile compound is selected from the group of ammonia and volatile amines.

74. The method of claim 73, wherein said volatile compound is ammonia.

75. The method of claim 62, wherein said pressure below a predetermined reference pressure is obtained in the evaporator, the shunt, the first condensing device and a further condensing device.

76. The method of claim 62, wherein said pressure in the evaporator below a predetermined reference pressure is in the range of from 0.1 to 1.0 bar.

77. The method of claim 76, wherein said pressure below a predetermined reference pressure in the first condensing device and in a further condensing device is about 0.2 bar.

78. The method of claim 76, wherein the pressure in the stripper unit is about 2.5 bar.

79. The method of claim 62, wherein the cold steam is obtained by heating aqueous liquid in the evaporator to a temperature of 50 to 80° C.

80. The method of claim 62, wherein the temperature of said first condensed aqueous liquid medium comprising volatile compounds and/or vapor not condensed by the first condensing device is 15-35° C.

81. The method of claim 62, wherein the temperature of a counter current of aqueous liquid in a further condensing device is 15-35° C.

82. The method of claim 62, wherein the temperature of said first condensed aqueous liquid medium comprising volatile compounds and/or of said aqueous liquid fraction comprising volatile compounds in the stripper unit is 80-170° C.

83. The method of claim 82, wherein the temperature is from about 100° C. to about 150° C.

84. The method of claim 62, wherein the temperature of a second condensed aqueous liquid and/or vapor not condensed by a second condensing device is 15-45° C.

85. The method of claim 62, wherein said aqueous liquid medium comprising volatile compounds comprises an amount of from 2.5 to 85 kg volatile compounds per m3 (cubic meter).

86. The method of claim 62, wherein the liquid medium comprising volatile compounds is liquid medium comprising organic materials.

87. The method of claim 62, wherein the cold volatile compounds-comprising steam comprises volatile compounds in a concentration of about 0.53 to 109% volatile compounds.

88. The method of claim 62, wherein said aqueous liquid medium comprising a reduced concentration of volatile compounds is directed to a bioreactor.

89. The method of claim 62, wherein biomasses selected from the group consisting of meat and bone meal, vegetable protein, molasses, vinasse, and combinations thereof are fermented.

90. The method of claim 89, wherein the amount of meat and bone meal fermented in a bioreactor comprises more than 2.5% of the total biomass by weight.

91. The method of claim 88, wherein the bioreactor is a mesophilic or thermophilic bioreactor.

92. The method of claim 62, wherein the heating process in the evaporator is conducted by using heat exchangers reusing heat from machines, engines or motor generators, or by adding to the evaporator warm waste aqueous liquids, or aqueous liquid obtained from a cooling/condensing device.

93. The method of claim 62, wherein the volatile compound is ammonia, and wherein said condensed aqueous, ammonia comprising liquid resulting from condensation in said second condensing device is of commercial fertiliser grade.

94. The method of claim 62, wherein said vapor not condensed by the second and/or second condensing device is directed to an air scrubber or directly to the atmosphere.

* * * * *